US006777184B2

(12) United States Patent
Nikiforov et al.

(10) Patent No.: US 6,777,184 B2
(45) Date of Patent: Aug. 17, 2004

(54) DETECTION OF NUCLEIC ACID HYBRIDIZATION BY FLUORESCENCE POLARIZATION

(75) Inventors: Theo T. Nikiforov, San Jose, CA (US); Sang Jeong, Mountain View, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 82 days.

(21) Appl. No.: 09/854,417

(22) Filed: May 11, 2001

(65) Prior Publication Data

US 2002/0037520 A1 Mar. 28, 2002

Related U.S. Application Data

(60) Provisional application No. 60/203,723, filed on May 12, 2000.

(51) Int. Cl.[7] .......................... C12Q 1/68; C12P 19/34; C12M 1/34; C07H 21/02; C07H 21/04
(52) U.S. Cl. .......................... 435/6; 435/7.1; 435/91.1; 435/91.2; 435/287.2; 536/22.1; 536/23.1; 536/24.3; 536/24.31; 536/24.32; 536/24.33
(58) Field of Search .......................... 435/6, 7.1, 91.1, 435/91.2, 287.2; 526/22.1, 23.1, 24.3–24.33

(56) References Cited

U.S. PATENT DOCUMENTS

| | | | |
|---|---|---|---|
| 4,390,403 A | 6/1983 | Batchelder | |
| 4,908,112 A | 3/1990 | Pace | |
| 5,126,022 A | 6/1992 | Soane et al. | |
| 5,498,392 A | 3/1996 | Wilding et al. | |
| 5,571,410 A | 11/1996 | Swedberg et al. | |
| 5,585,069 A | 12/1996 | Zanzucchi et al. | |
| 5,587,128 A | 12/1996 | Wilding et al. | |
| 5,593,838 A | 1/1997 | Zanzucchi et al. | |
| 5,603,351 A | 2/1997 | Cherukuri et al. | |
| 5,635,358 A | 6/1997 | Wilding et al. | |
| 5,637,469 A | 6/1997 | Wilding et al. | |
| 5,641,633 A | 6/1997 | Linn et al. | |

(List continued on next page.)

FOREIGN PATENT DOCUMENTS

| | | |
|---|---|---|
| WO | WO 96/04547 | 2/1996 |
| WO | WO 97/02357 | 1/1997 |
| WO | WO 98/00231 | 1/1998 |
| WO | WO 98/00705 | 1/1998 |
| WO | WO 98/00707 | 1/1998 |
| WO | WO 98/02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56956 | 12/1998 |
| WO | WO 99/00649 | 1/1999 |
| WO | WO 99/10735 | 3/1999 |
| WO | WO 99/12016 | 3/1999 |
| WO | WO 99/16162 | 4/1999 |
| WO | WO 99/19056 | 4/1999 |
| WO | WO 99/19516 | 4/1999 |
| WO | WO 99/29497 | 6/1999 |
| WO | WO 99/56954 | 11/1999 |
| WO | WO 00/09753 | 2/2000 |
| WO | WO 01/14064 | 3/2001 |

OTHER PUBLICATIONS

Saiki et al Nature vol. 324 pp. 163–166 1986.*

Arnheim & Levinson (Oct. 1, 1990) C&EN 36–47; The Journal of NIH Research (1991).

(List continued on next page.)

*Primary Examiner*—Jeffrey Siew
(74) *Attorney, Agent, or Firm*—Donald R. McKenna

(57) ABSTRACT

Methods, systems and assays are provided for FP detection of nucleic acid hybridization.

38 Claims, 21 Drawing Sheets

U.S. PATENT DOCUMENTS

| | | | |
|---|---|---|---|
| 5,699,157 A | | 12/1997 | Parce |
| 5,716,784 A | * | 2/1998 | Di Cesare ...................... 435/6 |
| 5,750,015 A | | 5/1998 | Soane et al. |
| 5,779,868 A | | 7/1998 | Parce et al. |
| 5,800,690 A | | 9/1998 | Chow et al. |
| 5,800,989 A | | 9/1998 | Linn et al. |
| 5,824,517 A | | 10/1998 | Cleuziat et al. |
| 5,842,787 A | | 12/1998 | Kopf-Sill et al. |
| 5,852,495 A | | 12/1998 | Parce |
| 5,869,004 A | | 2/1999 | Parce et al. |
| 5,876,675 A | | 3/1999 | Kennedy |
| 5,880,071 A | | 3/1999 | Parce et al. |
| 5,882,465 A | | 3/1999 | McReynolds |
| 5,885,470 A | | 3/1999 | Parce et al. |
| 5,942,443 A | | 8/1999 | Parce et al. |
| 5,948,227 A | | 9/1999 | Dubrow |
| 5,955,028 A | | 9/1999 | Chow |
| 5,957,579 A | | 9/1999 | Kopf-Sill et al. |
| 5,958,203 A | | 9/1999 | Parce et al. |
| 5,958,694 A | | 9/1999 | Nikiforov |
| 5,959,291 A | | 9/1999 | Jensen |
| 5,964,995 A | | 10/1999 | Nikiforov et al. |
| 5,965,001 A | | 10/1999 | Chow et al. |
| 5,965,410 A | | 10/1999 | Chow et al. |
| 5,972,187 A | | 10/1999 | Parce et al. |
| 5,976,336 A | | 11/1999 | Dubrow et al. |
| 5,989,402 A | | 11/1999 | Chow et al. |
| 6,001,231 A | | 12/1999 | Kopf-Sill |
| 6,004,515 A | | 12/1999 | Parce et al. |
| 6,011,252 A | | 1/2000 | Jensen |
| 6,012,902 A | | 1/2000 | Parce |
| 6,042,710 A | | 3/2000 | Dubrow |
| 6,046,056 A | | 4/2000 | Parce et al. |
| 6,068,752 A | | 5/2000 | Dubrow et al. |
| 6,071,478 A | | 6/2000 | Chow |
| 6,074,725 A | | 6/2000 | Kennedy |
| 6,080,295 A | | 6/2000 | Parce et al. |
| 6,280,946 B2 | * | 8/2001 | Hyldig-Nielsen et al. ...... 435/6 |
| 6,287,774 B1 | * | 9/2001 | Nikiforov ...................... 435/6 |
| 6,436,646 B1 | * | 8/2002 | Nikiforov ...................... 435/6 |

OTHER PUBLICATIONS

Cohen, C.B. et al., "A Microchip–Based Enzyme Assay for Protein Kinase A," *Anal. Chem.* (1999) 273:89–97.

Dasgupta, P.K. et al., "Electroosmosis: A Reliable Fluid Propulsion System for Flow Injection Analysis," *Anal. Chem.* (1994) 66:1792–1798.

Jacobson, S.C. et al., "Fused Quartz Substrates for Microchip Electrophoresis," *Anal. Chem.* (1995) 67:2059–2063.

Manz, A. et al., "Electroosmotic pumping and electrophoretic separations for miniaturized chemical analysis systems," *J. Micromech. Microeng.* (1994) 4:257–265.

Ramsey, J.M. et al., "Microfabricated chemical measurement systems," *Nature Med.* (1995) 1:1093–1096.

Seiler, K. et al., "Planar Glass Chips for Capillary Electrophoresis: Repetitive Sample Injection, Quantitation, and Separation Efficiency," *Anal. Chem.* (1993) 65:1481–1488.

Seiler, K. et al., "Electroosmotic Pumping and Valveless Control of Fluid Flow Within a Manifold of Capillaries on a Glass Chip," *Anal. Chem.* (1994) 66:3485–3491.

Sundberg, S. A., "High–throughput and ultra–high–throughput screening: solution—and cell–based approaches," *Current Opinions in Biotechnology* 2000, 11:47–53.

* cited by examiner

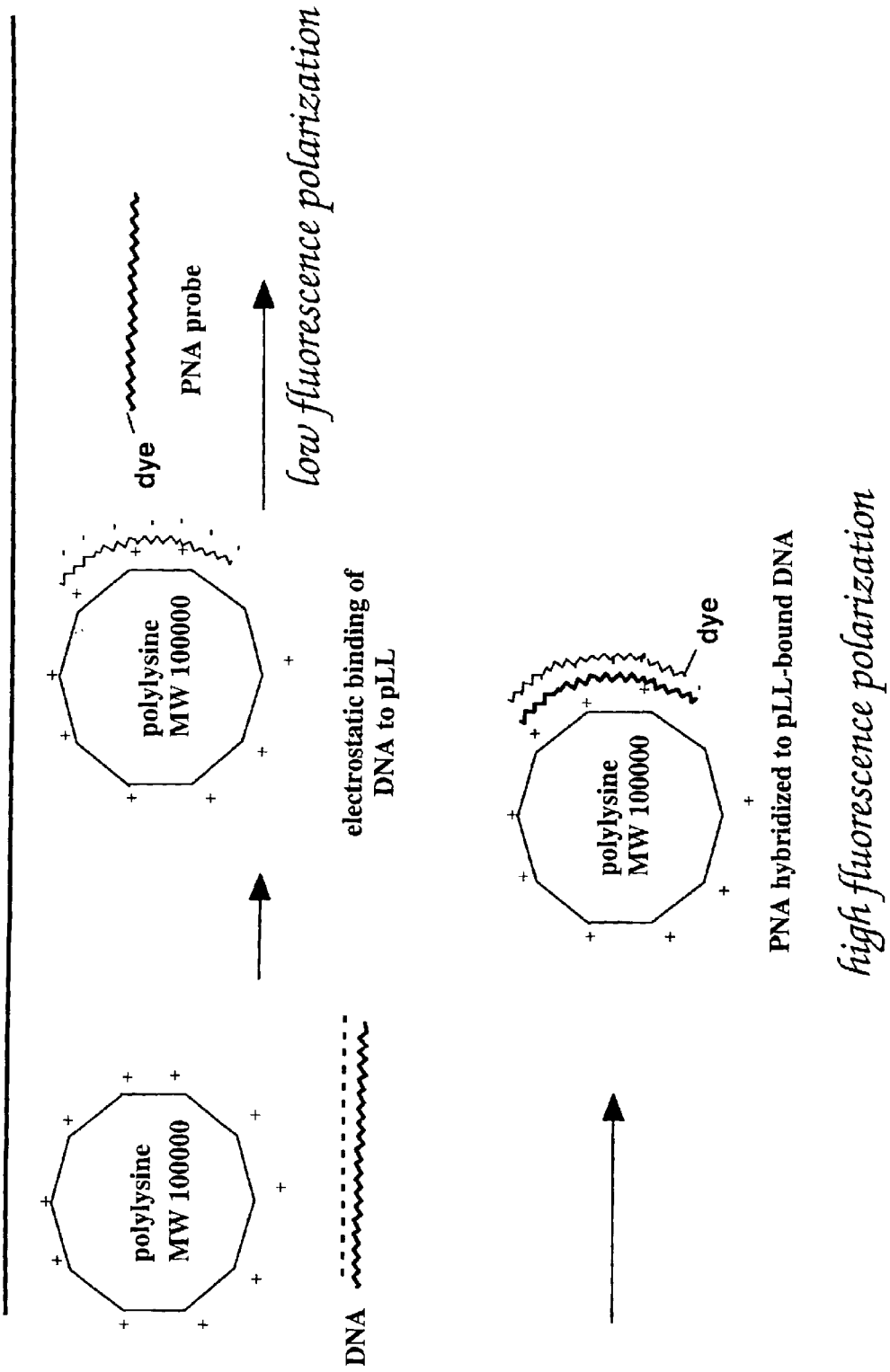

Rhodamine

Fluorescein

DETECTION OF NUCLEIC ACID HYBRIDIZATION BY FLUORESCENCE POLARIZATION

CROSS-REFERENCE TO RELATED APPLICATIONS

This application is a non-provisional of U.S. Ser. No. 60/203,723, filed May 12, 2000 entitled "DETECTION OF PNA/DNA FORMATION BY FLUORESCENCE POLARIZATION" by Theo T. Nikiforov, and Sang Jeong. The present application claims priority to and benefit of U.S. Ser. No. 60/203,723.

FIELD OF THE INVENTION

This invention is in the field of detection of fluorescence polarization, e.g., in microfluidic devices.

BACKGROUND OF THE INVENTION

Detection of single nucleotide polymorphisms (SNPs) and other genetic phenomena is an increasingly important technique in molecular biology and medicine. For example, in medical contexts, polymorphism detection is useful for diagnosing inherited diseases and susceptibility to diseases. The detection of SNPs and other polymorphisms can also serve as a basis for tailoring or targeting treatment, i.e., where certain allelic forms of a polymorphism are associated with a response to a particular treatment. In molecular biology, polymorphism detection is fundamental in a variety of contexts, including molecular marker assisted breeding (e.g., of important crop varieties such as Zea and other Graminea, soybeans, etc.), the study of gene diversity, gene regulation and other genetic, epigenetic or para-genetic phenomena.

Many techniques exist for measuring nucleic acid hybridization for polymorphism detection, as well as for other purposes. In addition to standard Southern and northern blotting, complex arrays of nucleic acid probes are available from a variety of commercial sources, as are solution based detection methods such as those utilizing fluorescence resonance energy transfer (FRET), molecular beacons, or other real-time solution-based hybridization detection methods. These hybridization methodologies typically involve the use of one or more probe, e.g., which includes a fluorophore or other label. Specific hybridization is detected by localization of probe label signals in solid phase hybridization methods such as Southern blotting, or array-based versions thereof, or by real time optical and/or spectroscopic methods which monitor changes in fluorescence in solution, e.g., as detected by FRET.

One additional technique has recently been used for detecting hybridization formation between nucleic acids, e.g., in the presence of polylysine. As described by the inventors in Nikiforov and Jeong "Detection of Hybrid Formation between Peptide Nucleic Acids and DNA by Fluorescence Polarization in the Presence of Polylysine" (1999) *Analytical Biochemistry* 275:248–253, Fluorescence Polarization (FP) provides a useful method to detect hybridization formation between nucleic acids. This method is applicable to hybridization detection, e.g., to monitor SNPs.

Generally, FP operates by monitoring the speed of rotation of fluorescent labels, such as fluorescent dyes, e.g., before, during and/or after binding events between probes which comprise the labels and target molecules. In short, binding of the probe to a target molecule ordinarily results in a decrease in the speed of rotation of the bound probe, resulting in a change in FP.

For example, when a fluorescent molecule is excited by a polarized light source, the molecule will emit fluorescent light in a fixed plane; that is, the emitted light is also polarized, provided that the molecule is fixed in space. However, because the molecule is typically rotating and tumbling in space, the plane in which the fluoresced light is emitted varies with the rotation of the molecule (also termed the rotational diffusion of the molecule). Restated, the emitted fluorescence is generally depolarized. The faster the molecule rotates in solution, the more depolarized it is. Conversely, the slower the molecule rotates in solution, the less depolarized, or the more polarized it is. The polarization value (P) for a given molecule is proportional to the molecule's "rotational correlation time," or the amount of time it takes the molecule to rotate through an angle of 57.3° (1 radian). The smaller the rotational correlation time, the faster the molecule rotates, and the less polarization will be observed. The larger the rotational correlation time, the slower the molecule rotates, and the more polarization will be observed. Rotational relaxation time is related to viscosity ($\eta$), absolute temperature (T), molar volume (V), and the gas constant (R). The rotational correlation time is generally calculated according to the following formula:

$$\text{Rotational Correlation Time} = 3\eta V/RT \quad (1)$$

As can be seen from the above equation, if temperature and viscosity are maintained constant, then the rotational relaxation time, and, therefore, the polarization value, is directly related to the molecular volume. Accordingly, the larger the molecule, the higher its fluorescent polarization value, and conversely, the smaller the molecule, the smaller its fluorescent polarization value.

In the performance of fluorescent binding assays, a typically small, fluorescently labeled molecule, e.g., a ligand, antigen, etc., having a relatively fast rotational correlation time, is used to bind to a much larger molecule, e.g., a receptor protein, antibody etc., which has a much slower rotational correlation time. The binding of the small labeled molecule to the larger molecule significantly increases the rotational correlation time (decreases the amount of rotation) of the labeled species, namely the labeled complex over that of the free unbound labeled molecule. This has a corresponding effect on the level of polarization that is detectable. Specifically, the labeled complex presents much higher fluorescence polarization than the unbound, labeled molecule.

Generally, the fluorescence polarization level is calculated using the following formula:

$$P = [I(\|) - I(\perp)]/[I(\|) + I(\perp)] \quad (2)$$

Where $I(\|)$ is the fluorescence detected in the plane parallel to the excitation light, and $I(\perp)$ is the fluorescence detected in the plane perpendicular to the excitation light.

In addition to Nikiforov and Jeong (1999), above, other references which discuss fluorescence polarization and/or its use in molecular biology include Perrin (1926). "Polarization de la lumiere de fluorescence. Vie moyenne de molecules dans l'etat excite." *J Phys Radium* 7, 390; Weber (1953) "Rotational Brownian motion and polarization of the fluorescence of solutions" *Adv Protein Chem* 8, 415; Weber (1956). *J Opt Soc Am* 46, 962; Dandliker and Feigen (1961), "Quantification of the antigen-antibody reaction by the polarization of fluorescence" *Biochem Biophys Res Commun* 5, 299; Dandliker and de Saussure (1970) (Review Article) "Fluorescence polarization in immunochemistry" *Immunochemistry* 7, 799; Dandliker W B, et al. (1973).

"Fluorescence polarization immunoassay. Theory and experimental method." *Immunochemistry* 10, 219; Levison S A, et al. (1976), "Fluorescence polarization measurement of the hormone-binding site interaction" *Endocrinology* 99, 1129; Jiskoot et al. (1991), "Preparation and application of a fluorescein-labeled peptide for determining the affinity constant of a monoclonal antibody-hapten complex by fluorescence polarization" *Anal Biochem* 196, 421; Wei and Herron (1993), "Use of synthetic peptides as tracer antigens in fluorescence polarization immunoassays of high molecular weight analytes" *Anal Chem* 65, 3372; Devlin et al. (1993), "Homogeneous detection of nucleic acids by transient-state polarized fluorescence" *Clin Chem* 39, 1939; Murakami et al. (1991), Fluorescent-labeled oligonucleotide probes detection of hybrid formation in solution by fluorescence polarization spectroscopy." *Nuc. Acids Res* 19, 4097. Checovich et al. (1995), "Fluorescence polarization-a new tool for cell and molecular biology" (product review), *Nature* 375, 354–256; Kumke et al. (1995), "Hybridization of fluorescein-labeled DNA oligomers detected by fluorescence anisotropy with protein binding enhancement" *Anal Chem* 67:21, 3945–3951; and Walker et al. (1996), "Strand displacement amplification (SDA) and transient-state fluorescence polarization detection of mycobacterium tuberculosis DNA" *Clinical Chemistry* 42:1, 9–13.

One difficulty in the use of FP to monitor hybridization of nucleic acids is that the change in FP which occurs simply upon binding of a labeled probe to a complementary nucleic acid has previously been observed to be small. Thus, helper molecules such as DNA binding proteins or polycations are used to increase the change in FP (and, therefore, the dynamic range of the assay) which is observed upon hybridization of nucleic acids (e.g., by binding to the hybridized nucleic acid, thereby increasing the size of the complex). While increasing the dynamic range of the assay, this approach also increases the complexity of the assay and secondary effects caused by helper molecules can bias the assay.

Quite surprisingly, the present invention overcomes these previous difficulties, providing a robust assay for direct detection of nucleic acid hybridization by monitoring changes in FP.

SUMMARY OF THE INVENTION

It has, quite surprisingly, been discovered that the use of neutral or positively charged fluorescent labels on nucleic acid probes results in a relatively large change in observed FP of the probe label during nucleic acid hybridization. Thus, probes (e.g., PNAs, DNAs, LNAs, RNAs or other nucleic acids, or even other nucleic acid binding moieties) can be labeled with neutral or positively charged fluorescent dyes such as rhodamine or BODIPY and FP can effectively be used to monitor hybridization of such labeled probes to target nucleic acids. This surprising discovery provides the basis for simplified and less biased FP assays than those used in the past.

Accordingly, the present invention provides methods of performing nucleic acid hybridization analysis (i.e., using probes comprising neutral or positively charged fluorescent dyes). This analysis is useful, e.g., for polymorphism detection, as well as for many other applications.

In addition to providing new methods, the present invention provides assay systems, kits, computer implemented processes and microfluidic systems for practicing the methods of the invention. For example, assay systems with containers comprising probes comprising neutral or positively charged fluorescent dyes are a feature of the present invention, e.g., in combination with apparatus for performing FP measurements.

BRIEF DESCRIPTION OF THE FIGURES

FIG. 4, shows additional histograms and example conclusions for the effect of polylysine on DNA/PNA duplex stability, real time detection of T7 gene 6 exonuclease degradation of a PCR product coupled with PNA probe hybridization and the effect of target size and polylysine.

DETAILED DISCUSSION OF THE INVENTION

Figure 1:
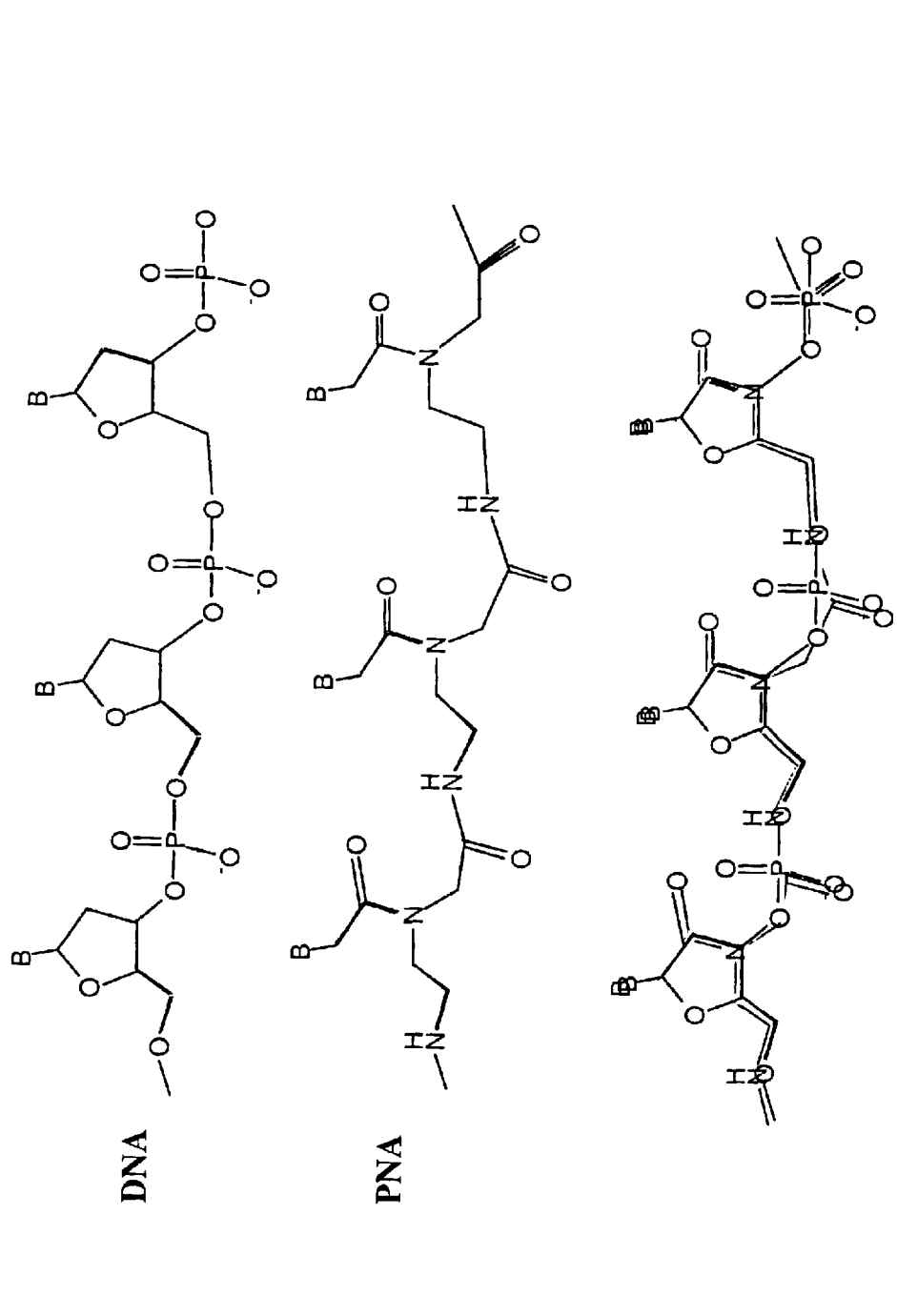
FIG. 1 is a schematic representation of DNAs and PNAs. The top is a schematic of a single stranded DNA. The middle is a schematic of a single-stranded PNA. The bottom is a schematic overlay of the DNA and PNA, showing the similarity of the overall structure of the two molecules.

DNA/DNA hybrids have been detected by FP, but the observed changes in FP were quite low (10–30 mP). To increase the dynamic range of FP assays which examine DNA—DNA hybridization, DNA-binding proteins (for example, mutant versions of EcoR1) have been used to increase the dynamic range of the assays of interest. More recently, hybridization formation between, e.g., PNAs and DNAs, have been examined by FP, in the presence of polylysine ("Detection of Hybrid Formation between Peptide Nucleic Acids and DNA by Fluorescence Polarization in the Presence of Polylysine" (1999) *Analytical Biochemistry* 275:248–253). Additional details are found in U.S. patent application Ser. No. 09/316,447, filed May 21, 1999, and Provisional Patent Application No. 60/139,562, filed Jun. 16, 1999 and No. 60/156,366, filed Sep. 28, 1999.

The present invention relates to a new way of examining nucleic acid hybridization by FP which does not rely on the use of proteins or polycations to increase the dynamic range of the hybridization assays. In particular, it is surprisingly discovered that the use of neutral or positively charged fluorophores as labels on nucleic acid probes such as PNAs or LNAs results in large changes in FP upon hybridization of the probe to a target nucleic acid.

As noted above, FP is calculated, e.g., using the following formula:

$$P=[I(\|)-I(\perp)]/[I(\|)+I(\perp)] \quad (2)$$

Where $I(\|)$ is the fluorescence detected in the plane parallel to the excitation light, and $I(\perp)$ is the fluorescence detected in the plane perpendicular to the excitation light.

Fluorescence polarization depends on molecular size. For example the "Perrin" equation shows the relationship between FP and molecular size:

$$(1/P-1/3)=(1/P_0-1/3)(1-3\tau/P) \quad (3)$$

Where P is the rotational relaxation time for a sphere; $\tau$ is the fluorescence decay time and P and $P_0$ are the measured and the so-called "limiting" polarization value. Thus, where nucleic acids are hybridized, there should be a change in FP due to the difference in the overall size of hybridized molecules relative to unhybridized molecules. The present invention provides for the detection of changes in FP that result from hybridization of nucleic acids, where at least one of the nucleic acids is labeled with a neutral or positively charged fluorescent dye. The inclusion of such a dye results in a substantial change in FP. This detection of hybridization is useful for genotyping samples, detecting polymorphisms, verifying nucleic acid sequences and any other assay or technique that utilizes nucleic acid hybridization as a mechanism for detecting an event of interest.

Methods, Apparatus and Systems of the Invention—Overview

As noted, methods for detecting a nucleic acid are provided by the present invention. In a basic form of the methods, a first nucleic acid (e.g., a target nucleic acid derived from a biological source) is contacted to a second nucleic acid (e.g., a probe) which comprises a neutral or positively charged fluorescent label. Fluorescence polarization of the resulting mixture of first and second nucleic acids is then detected.

As noted, the observed difference in FP is relatively large upon hybridization of probes comprising a neutral or positively charged fluorescent label, avoiding the need for the addition of FP enhancers (polycations, DNA binding proteins, etc.) to enhance the dynamic range of the change in FP. Furthermore, because the difference in FP is relatively large upon hybridization of the probe and target, the addition of enhancers such as DNA binding proteins or polyions has a relatively modest effect on FP. For example, the difference in fluorescence polarization which occurs for a probe upon hybridization to a target nucleic acid is typically increased by less than about 50% (and often by less than about 40%, 30%, 20%, or even less than about 10%) by the addition of enhancers such as polylysine as compared to FP in the absence of polylysine.

Restated, a change in FP is observed when a first nucleic acid and a second nucleic acid comprising a positive or neutral fluorophore are hybridized ($\Delta x_1$). In the present invention, a change in FP is also observed when the first nucleic acid and the second nucleic acid are hybridized in the presence of polylysine ($\Delta x_2$). In the present invention, $\Delta x_1$ is typically at least 50% as large as $\Delta x_2$, and $\Delta x_1$ is typically at least about 60%, 70%, 80%, or even about 90% or more as large as $\Delta x_2$. This is in contrast to the use of probes comprising dyes such as fluorescein, which show dramatic increases in FP by the addition of polyions. In general, the change in FP when using neutral or positively charged dyes according to the present invention results in a relatively smaller change in FP as compared to the use of a probe which is labeled with fluorescein. Accordingly, an advantage of the present invention is that hybridization can be performed in compositions which are substantially free of FP enhancers such as polyions or DNA binding proteins. This a useful feature, e.g., when using DNA binding proteins in reducing binding of analyte material to walls of a channel in a flowing microfluidic context, as well as in generally reducing biasing of the assay due to binding protein effects. For example, hybridization compositions optionally comprise binding protein or polyion concentrations of less than about 1 $\mu$M, and generally about 0.5 $\mu$M or less, often about 0.1 $\mu$M or less, or even less than 0.01 M. For purposes of the present disclosure, the term "substantially no FP enhancer" in reference to a mixture refers to a mixture having a concentration of less than 0.001 $\mu$M enhancer (e.g., polyion, DNA binding protein, etc.).

Rotational diffusion rates of a duplex of the first and second nucleic acid is less than a rotational diffusion rate of the first or second nucleic acid. Typically, the fluorescence polarization of unduplexed first or second nucleic acid is at least 25% different than the fluorescence polarization of the duplexed nucleic acid (and can be about 50%, about 60%, about 70% or about 80% or more different).

In the present invention, the nucleic acids which can be hybridized include any available form of a nucleic acid, including DNA, RNA, DNA analogues, RNA analogues, PNAs, LNAs, etc., or mixtures thereof.

A peptide nucleic acid (PNA) is a polymer of peptide nucleic acid monomers. The polymer can additionally comprise elements such as labels, quenchers, blocking groups, or the like. The monomers of the PNA can be substituted or modified. A locked nucleic acid (LNA) is any of a variety of structurally constrained polynucleotides. These LNAs can often bind to DNAs or other nucleic acids with higher avidity, affinity, and/or specificity than corresponding standard DNAs. Typically, LNA monomers are bicyclic compounds structurally similar to RNA nucleosides. The term "Locked Nucleic Acid" has been coined to emphasize that the furanose ring conformation can be restricted in a typical LNA by a methylene linker that connects the 2'-O position to the 4'-C position. For convenience, nucleic acids containing one or more LNA modifications are optionally referred to as LNAs. LNA oligomers obey Watson-Crick base pairing rules and hybridize to complementary DNA, RNA or PNA oligonucleotides.

The term "nucleic acid" encompasses any physical string of monomer units that can be corresponded to a string of nucleotides, including a polymer of nucleotides, PNAs, LNAs, modified oligonucleotides and the like. For example, a "nucleic acid" in the context of the present invention is a polymer of monomer units which has sufficient structural similarity to a complementary DNA, RNA, LNA, or PNA that it can bind to such a molecule in solution with an affinity that is at least about 10% (and often about 50% or more) as high as a fully complementary DNA, RNA, LNA, or PNA. Common nucleic acids, as used herein, include DNAs, RNAs, LNAs, PNAs and many modified forms of these molecules, e.g., where the modifications provide for nuclease resistance (e.g., by methylation), detection (e.g., by labeling) or other features of interest.

In one embodiment, one or more of the nucleic acids is nuclease resistant. Examples of nuclease resistant nucleic acids include PNAs, LNAs, methylated nucleic acids, methyl phosphonate polymers, cationic nucleic acid analogs, and many others. As noted, fluorescent labels include rhodamine and BODIPY. For example, the first nucleic acid can be a target nucleic acid such as a DNA or RNA isolated or derived from a biological sample, while the second nucleic acid can be, e.g., a probe nucleic acid comprising a PNA (or a DNA, LNA, or RNA, etc.), e.g., comprising a rhodamine label.

Although triplex nucleic acids, Z DNA and other relatively unusual variant forms of nucleic acids are optionally detected by the methods herein, it is most commonly the case that both the first or second nucleic acid (e.g., target and probe) will include at least a region of single-stranded nucleic acid to provide the possibility of standard Watson-Crick base-pair mediated hybridization to a complementary molecule. For example, the first and second nucleic acid can be partly or perfectly complementary to allow for hybridization. The nucleic acids can also be partly or completely non-complementary, e.g., where one nucleic acid corresponds to a first allele and the second nucleic acid corresponds to a different allele of a nucleic acid locus.

In addition to determining from fluorescence polarization detection whether the first and second nucleic acids are duplexed (e.g., hybridized) in any fashion, the present invention can also be used to determine qualitative hybridization information. For example, in one aspect, the invention provides for determining the extent to which the first and second nucleic acids are duplexed by measuring fluorescence polarization following probe binding to a first target as compared to one or more additional targets or controls. Thus, for example, where the first and second nucleic acids hybridize in solution prior to detection of fluorescence polarization, the method can include comparing the detected fluorescence polarization to a fluorescence polarization measurement of either the first or the second nucleic acid alone in solution, or comparing the detected fluorescence polarization to a fluorescence polarization measurement of either the first or the second nucleic acid hybridized to a third nucleic acid. For example, the third nucleic acid can be a control which is perfectly complementary to either the first or the second nucleic acid. Alternately, the third nucleic acid can be a negative control which is not complementary to either the first or the second nucleic acid, e.g., where the third nucleic acid is unrelated in sequence to either the first or the second nucleic acid. Competitive formats, in which perfectly matched (or unmatched) probes are shown to compete (or not to compete) with a probe of interest can also be used to monitor duplex formation.

Commonly, time-course FP measurements are taken to provide hybridization profiles, to provide kinetic information or to examine other features of hybridization. Thus, fluorescence polarization of the mixture or components thereof can be detected before, during and/or after hybridization of the first and second nucleic acid. Fluorescence polarization can be measured as a function of time during hybridization of the first and second nucleic acid. Common representations of the data produced in such hybridization experiments include graphical representations (e.g., any histogram), data tables and the like. Computer implementations of data capture and manipulation are preferred in the context of the present invention.

In an especially relevant embodiment, the present invention provides a method of detecting or identifying the presence or absence of a subsequence of nucleotides in a target nucleic acid, or in a set of target nucleic acids (e.g., a DNA or RNA sample isolated from a biological source). In the method, the target nucleic acid sequence is contacted with a labeled nucleic acid probe, which labeled nucleic acid probe comprises a neutral or positively charged label comprising a fluorophore to form a first reaction mixture. The level of fluorescence polarization of the first reaction mixture is, typically, detected.

As noted, one useful embodiment involves using this method to detect single nucleotide polymorphisms. In this embodiment, the target nucleic acid comprises at least one locus comprising at least one nucleotide polymorphism. For example, the nucleic acid probe is optionally fully complementary to one allele of the single nucleotide polymorphism in the target nucleic acid sequence, but not another. Comparative measurements between hybridization experiments with probes that preferentially hybridize to different alleles can also be used to identify which allele a given target nucleic acid corresponds to.

In one aspect, the invention provides a method of genotyping a nucleic acid sample. Typically, this involves hybridizing (serially or in parallel) a number of different probes to one or more target nucleic acids (e.g., derived from a single biological source). The information generated by multiple target-probe interactions corresponds to a genotype for the sample. For example, in addition to the target-probe interactions set forth above, the invention can include contacting a plurality of additional target nucleic acids with a plurality of additional labeled nucleic acid probes, which individually comprise a neutral or positively charged label comprising a fluorophore, to form a plurality of additional reaction mixtures. The level of fluorescence polarization of the plurality of additional reaction mixtures is then detected. The plurality of additional target nucleic acids can individually comprise one or more locus for one or more SNP (or other polymorphism). The plurality of additional nucleic acid probes are, for example, each complementary to one allele of each of the single nucleotide polymorphisms in the plurality of target nucleic acid sequences. The biological source of the nucleic acid can be, e.g., a single species, variety, cultivar, organism, cell, virus, or any other appropriate source. Identification of the single nucleotide polymorphisms provides, e.g., a single nucleotide polymorphism genotype for the species, variety, cultivar, cell, virus or organism.

The present invention also provides systems for practicing the methods set forth herein. An system of the invention includes, e.g., a container comprising a duplexed nucleic acid disposed in the container, where at least one strand of the nucleic acid duplex comprises a neutral or positively charged fluorescent label. The system further includes a polarized light source positioned to shine plane polarized light through a portion of the container, thereby exciting the fluorescent label during operation of the system. A detector that detects resultant polarization of light emitted by the fluorescent label is typically positioned proximal to the container.

In a preferred aspect, the container comprises a microfluidic device which contains the duplexed nucleic acid in one or more channels or chambers of the device. Microfluidic devices are particularly well-suited to high throughput analysis of reagents, e.g., in SNP genotyping applications. Thus, in one aspect, the microfluidic device comprises a body structure having two or more intersecting microchannels disposed therein, a source of the first nucleic acid and a source of a second nucleic acid. The sources are in fluid communication with the at least two intersecting microchannels, and, during operation of the device, the first nucleic acid is flowed from the source of the first nucleic acid into at least one of the at least two intersecting channels and the second nucleic acid is flowed from the source of the second nucleic acid into the at least one channel, whereby the first and second nucleic acids are mixed in the at least one channel. The detector is, e.g., positioned proximal to the at least one channel to detect fluorescence (e.g., FP) from the channel.

In general, the optional features noted above for the methods of the invention have corresponding elements in the systems of the invention, e.g., with respect to composition of the nucleic acid mixtures, probes, activities and the like.

As already noted, microfluidic applications of the present invention (e.g., detection of FP measurements in a microfluidic system) are particularly preferred. Thus, in one aspect, the invention provides a microfluidic fluorescent polarization nucleic acid analysis system. For example, in one simple version, the system includes a microfluidic device comprising a body structure having one or more, and optionally at least two microfluidic channels disposed therein, a source of a first nucleic acid, a source of a second labeled nucleic acid which comprises a neutral or positively charged fluorescent label, a source of plane polarized light, which is positioned to illuminate a portion of at least one of the at least two microchannels and a fluorescence polarization detector positioned to detect plane polarized light emitted from the microfluidic device.

In another aspect, the invention provides computer implemented processes. For example, computer implemented processes can be used in an assay system for quantifying a nucleic acid hybridization parameter. For example, in the overall process of providing a first nucleic acid composition comprising a first nucleic acid having a positive or neutral fluorescent label, introducing a second nucleic acid into the first nucleic acid composition to produce a second nucleic acid composition, reacting the second nucleic acid with the first nucleic acid to produce a fluorescently labeled product having a substantially different rotation rate than the first nucleic acid, a computer implemented process can be used. For example, the computer implemented process can include determining, in a computer, a first level of fluorescence polarization of the first nucleic acid composition; determining a second level of fluorescence polarization of the second nucleic acid composition; and, comparing the first and second levels of fluorescent polarization; and calculating the nucleic acid hybridization parameter.

Kits for practicing the methods herein, e.g., comprising any of the compositions or systems herein with containers and instructional materials for practicing the methods are also a feature of the invention.

Making Nucleic Acids

In the present invention, a probe nucleic acid is typically hybridized to a target nucleic acid. Either nucleic acid can be derived from a biological source, or made synthetically, or both. The probe nucleic acid comprises a positive or neutral fluorescent label.

General texts which describe the isolation, synthesis, cloning and amplification of nucleic acids from biological sources, including the use of vectors, promoters and many other relevant topics, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1–3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 2000) ("Ausubel")). Examples of techniques sufficient to direct persons of skill through in vitro amplification methods, including the polymerase chain reaction (PCR) the ligase chain reaction (LCR), Qβ-replicase amplification and other RNA polymerase mediated techniques (e.g., NASBA), e.g., for the production or isolation of the nucleic acids of the invention are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Amheim & Levinson (Oct. 1, 1990) *C&EN* 3647; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684–685 and the references therein, in which PCR amplicons of up to 40 kb are generated.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

The polynucleotides of the invention (particularly probes) can also be prepared by chemical synthesis using, e.g., the classical phosphoramidite method described by Beaucage et al., (1981) *Tetrahedron Letters* 22:1859–69, or the method described by Matthes et al., (1984) *EMBO J.* 3: 801–05, e.g., as is typically practiced in automated synthetic methods. According to the phosphoramidite method, oligonucleotides are synthesized, e.g., in an automatic DNA synthesizer, and, optionally purified, annealed, ligated, cloned amplified or otherwise manipulated by standard methods to produce additional nucleic acids.

The modifications to such protocols to accommodate non-natural monomers such as PNAs or LNAs are well known. For LNAs, see also, proligo.com; Koshkin et al. (1998) *Tetrahedron* 54:3607–3630; Koshkin et al. (1998) *J. Am. Chem. Soc.* 120:13252–13253; Wahlestedt et al. (2000) *PNAS.* 97:5633–5638. For PNAs see also, bostonprobes.com; and Buchardt et al. (1993) "Peptide nucleic acids and their potential applications in biotechnology" *TIBTECH.* 11:384–386; Corey (1997) "Peptide nucleic acids: expanding the scope of nucleic acid recognition" *TIBTECH* 15:224–229; Dueholmand and Nielsen (1997) "Chemistry, properties and applications of PNA" *New J. Chem.* 21:19–31; Hyrup and Nielsen "Peptide Nucleic Acids (PNA): Synthesis, Properties and Potential Applications" *Bioorg. Med. Chem.* 4:5–23; Nielsen et al. (1994) "Peptide Nucleic Acid (PNA). A DNA mimic with a peptide backbone" *Bioconjugate Chemistry* 5:3–7; Nielsen (1995) "DNA analogues with nonphosphodiester backbones" *Annu. Rev. Biophys. Biomol. Struct.* 24:167–183; Nielsen et al. (1993) "Peptide nucleic acids (PNA): oligonucleotide analogs with a polyamide backbone" *Antisense Research and Applications* (eds Crooke and Lebleu) 364–373 CRC Press; Nielsen (1999) "Peptide nucleic acid. A molecular with two identities" *Acc. Chem. Res.* 32: 624–630; Ørum et al. (1997) "Peptide Nucleic Acid" *Laboratory Methods for the Detection of Mutations and Polymorphisms in DNA* Chapter 11 (ed. Taylor, G. R.) 123–133 (1997); and Ørum et al. (1997) "Peptide Nucleic Acid" *Nucleic Acid Amplification Technologies: Applications to Disease Diagnostics.* (ed. Lee et al.) pp. 29–48.

In addition, essentially any nucleic acid (and virtually any labeled nucleic acid) can be custom or standard ordered from any of a variety of commercial sources, such as The Midland Certified Reagent Company (mcrc@oligos.com), The Great American Gene Company (http://www.genco.com), ExpressGen Inc. (www.expressgen.com), Operon Technologies Inc. (Alameda, Calif.) and many others. PNAs are generally commercially available, e.g., from the Applied Biosystems Division of the Perkin-Elmer Corporation (Foster City, Calif.). PNAs are also available, e.g., from Boston Probes Inc. (Bedford, Mass.). LNAs are available, e.g., from Proligo LLC (Boulder, Colo.).

As noted, essentially any nucleic acid or nucleic acid analogue can be used in the context of the present invention, including DNAs, LNAs, RNAs, PNAs and analogues thereof. One of skill will be fully aware of many different analogues and methods for making such analogues. Additional details on certain analogues, including certain nuclease resistant analogues, are found in e.g., Egholm, M. et al., (1993) *Nature* 365:566–568; Perry-O'Keefe, H. et al., (1996) *Proc. Natl. Acad. USA* 93:14670–14675; Miller, et al., "Nonionic nucleic acid analogues. Synthesis and characterization of dideoxyribonucleoside methylphosphonates", *Biochemistry* 1979, 18, 5134–5143. Divakar, et al., "Approaches to the Synthesis of 2'-Thio Analogues of Pyrimidine Ribosides", *J. Chem. Soc., Perkins Trans.*, I, 1990, 969–974; U.S. Pat. No. 5,872,232 to Cook, et al. "2'-O-modified oligonucleotides" and many other references known to one of skill.

Labels

As noted, probe nucleic acids are labeled with neutral or positively charged labels. Essentially any fluorophore can be made into a neutral or positively charged label, either by virtue of the fluorophore's intrinsic charge, or by incorporating a positively charged linker such as one or more lysine residues between the fluorophore and the probe nucleic acid.

The fluorescent label on the probe nucleic acid is optionally selected from any of a variety of different fluorescent labeling compounds. Generally, such fluorescent labeling materials are commercially available from, e.g., Molecular Probes (Eugene, Oreg.). Literally thousands of appropriate labels are commercially available. See, Haugland (1999) *Handbook of Fluorescent Probes and Research Chemicals* Seventh Edition by Molecular Probes, Inc. (Eugene Oreg.). See also, Haugland (1996) *Handbook of Fluorescent Probes and Research Chemicals* Published by Molecular Probes, Inc., Eugene, Oreg.) or a more current on-line (www.probes.com) or CD-ROM version of the Handbook (available from Molecular Probes, Inc.). Fluorescent labels are also commercially available from, e.g., The SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as other commercial sources known to one of skill.

Typically, rhodamine and BODIPY®-FL derivatives are particularly well suited to the assay methods described herein. These fluorescent labels are coupled, e.g., to the first reagent used in a nucleic acid synthesis protocol (e.g., a terminal nucleotide), e.g., covalently through well known coupling chemistries. For a discussion of labeling groups and chemistries, see, e.g., Published International Patent Application No. WO 98/00231, which is incorporated herein by reference. See also, *The Molecular Probes Handbook* (above); Henegariu et al. (2000) "Custom fluorescentnucleotide synthesis as an alternative method for nucleic acid labeling" *Nature Biotechnology* 18 (3): 345–348; Keller and Manak (1993) *DNA Probes, Second Edition* (Macmillan Publishers Ltd., England); and Green (1990) *The Sigma Aldrich Handbook of Stains, Dyes and Indicators* (Aldrich Chemical CO. Milwaukee, Wis.).

In addition to rhodamine and BODIPY, many other neutral or positively charged dyes are available. Indeed, as noted, even dyes which ordinarily have a net negative charge, such as many fluorescein derivatives, can be used in the context of the present invention simply by incorporating a positively charged linker (e.g., lysine or polylysine) to yield a fluorescent label with an overall positive charge. Fluorophore labels that can be used in the context of the present invention, optionally with linking groups to change the overall charge of the label to a neutral or positive state, include BODIPY-FL dyes, cascade blue dyes, fluorescein dyes, Oregon green dyes, rhodamine dyes (including rhodamine green dyes, tetramethylrhodamine dyes, Texas red dyes, and many others known to one of skill and available, e.g., from Molecular Probes, supra. Probes incorporating dyes can be made by standard synthetic techniques, as noted, or can be custom ordered from any of a variety of commercial sources. Commonly, base residues comprising dyes are added to the ends of probes by standard synthetic methods. Alternately, dyes can be added to probes by standard dye-nucleic acid or linker-dye-nucleic acid coupling methods. Many such techniques are available, both for the synthesis of nucleic acids such as DNA, LNA, or RNA which incorporate a ribose/deoxy ribose phospohodiester backbone and those such as PNAs which utilize amide bonding. Nucleic acids labeled with essentially any label of choice can also be ordered from any of a variety of commercial sources, including those noted above.

Assays of Interest

As noted, the present invention utilizes FP to detect specific hybridization interactions. Assays of interest can include essentially any nucleic acid hybridization experiment. Assays of particular interest include polymorphism detection (e.g., SNP detection), genotyping (e.g., by producing a set of information corresponding to multiple SNP detections) and other sequence verification experiments. As discussed in more detail below, these can be performed in the assay systems of the invention, including, especially, microfluidic assay formats.

Generally speaking, nucleic acids "hybridize" when they associate, e.g., in solution or partially in a solid phase (e.g., when one of the hybridizing nucleic acids is fixed on a solid support). Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, N.Y.), as well as in Ausubel, supra. Hames and Higgins (1995) *Gene Probes* 1 IRL Press at Oxford University Press, Oxford, England, (Hames and Higgins 1) and Hames and Higgins (1995) Gene Probes 2 IRL Press at Oxford University Press, Oxford, England (Hames and Higgins 2) provide additional details on the synthesis, labeling, detection and quantification of DNA and RNA, including oligonucleotides. Comparative hybridization is a common way of identifying specific nucleic acid interactions. There are many genetic markers that can be detected by hybridization. These include restriction fragment length polymorphisms (RFLPs), allele specific hybridization (ASH), single nucleotide polymorphism (SNP), arbitrary fragment length polymorphisms (AFLP), specific sequence detection (e.g., in sequencing by hybridization or sequence verification by hybridization) and many others.

In SNP and other sequence identification/verification assays, allele specific hybridization is detected, often in a comparative format. That is, a first hybridization reaction is typically performed and the change in FP due to hybridization (or lack of hybridization) is monitored. A second hybridization reaction is also performed and the change in FP due to hybridization (or lack of hybridization) is monitored. For example, the first hybridization reaction can involve hybridization of perfectly matching nucleic acids, e.g., which correspond to a polymorphic locus, while the second hybridization reaction can utilize the same target nucleic acid with a different probe nucleic acid (e.g., a probe which corresponds to a different allele of the locus). In this case, the change in FP in the first hybridization reaction due to hybridization is greater than the change in FP due to hybridization in the second reaction, because the nucleic acids in the first reaction are more complementary and, therefore, display a greater degree of hybridization.

Indeed, an assay such as that just outlined can be performed with known nucleic acids, e.g., to calibrate a system of interest. That is, the above comparative experiment can be performed under several hybridization conditions (different buffers, temperatures, etc.) until maximal comparative difference conditions for the reaction are identified. The reaction can then be repeated using targets of unknown sequence with respect to the polymorphism to identify probes which are matched (or not matched) to the target sequence (thereby identifying which variant the target nucleic acid corresponds to).

Thus, one aspect of the invention involves the use of control probes or control target nucleic acids, or both. The controls can be perfectly complementary to a sequence of relevance (a positive control), partly complementary (an intermediate control that helps establish how imperfectly matching alleles trigger changes in FP), or completely divergent (a negative control that separates out background FP changes due to non-specific hybridization).

Several different hybridization reactions can be run, serially or in parallel, to identify the genotype of a sample with respect to several different polymorphisms of interest. The genotype can be tracked digitally, e.g., in the systems below, to provide a compendium of the sequences of interest.

Integrated Assay Systems

The present invention provides systems, including microfluidic systems, for performing FP measurements for DNA hybridization experiments, i.e., using a probe comprising a neutral or positively charged fluorescent label.

Typically, the assay systems described herein comprise a fluid container/receptacle into which reagents (e.g., target and probe nucleic acids, with any appropriate accompanying buffers) are placed for performing the assay. The fluid container/receptacle optionally comprises a first reaction zone having disposed therein a first reagent mixture which comprises a first nucleic acid having a fluorescent label, and a second nucleic acid that hybridizes with the first nucleic acid to produce a fluorescently labeled product displaying a substantially different FP than the first labeled nucleic acid. The second nucleic acid has a neutral or positively charged fluorescent label.

Figure 5:
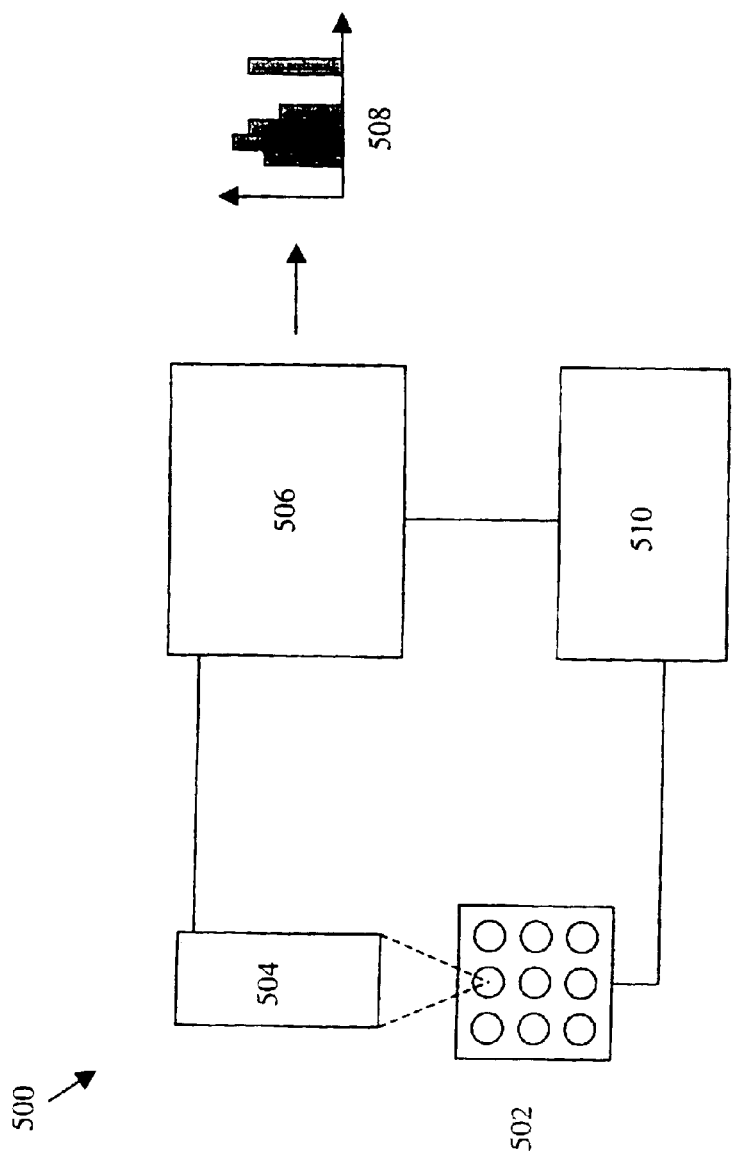
FIG. 5 is a schematic illustration of an overall system used to carry out the assay methods of the present invention.

FIG. 5 schematically illustrates an overall assay system which can be adapted to detect FP measurements according to the present invention. Briefly, the overall system 500 includes reaction container 502, as described above. Detector or detection system 504 is disposed adjacent to the container and within sensory communication of the container. The phrase "within sensory communication" generally refers to the relative location of the detector that is positioned relative to the container so as to be able to receive a particular signal from that container. In the case of optical detectors, e.g., fluorescence or fluorescence polarization detectors, sensory communication typically means that the detector is disposed sufficiently proximal to the container that optical, e.g., fluorescent signals are transmitted to the detector for adequate detection of those signals. Typically this employs a lens, optical train or other detection element, e.g., a CCD, that is focused upon a relevant portion of the container to efficiently gather and record these optical signals.

Detector 504 is typically connected (physically or logically) to an appropriate data storage and/or analysis unit, e.g., a computer or other processor, which is generally capable of storing, analyzing and displaying the obtained data from the receptacle in a user comprehensible fashion, e.g., as in display 508. In certain embodiments, e.g., those employing microfluidic receptacles, computer 506 is optionally connected to controller unit 510, which controls the movement of fluid materials within the channels of the microfluidic device receptacle, and/or controls the relative position of receptacle 502 and detector 504, e.g., via an x-y-z translation stage. The controller can use any fluid movement mechanism, including pressure, electrokinetic force, or the like.

The container also typically includes a detection zone as well as a detector disposed in sensory communication with the detection zone. The detector used in accordance with the present invention typically is configured to detect a level of fluorescence polarization of reagents in the detection zone.

As used herein, the container optionally take on any of a variety of forms. For example, the container is optionally a simple reaction vessel, well, tube, cuvette, or the like. Alternatively, the receptacle optionally comprises a capillary or channel either alone or in the context of an integrated fluidic system that includes one or more fluidic channels, chambers or the like.

In the case of a simple reaction vessel, well, tube, cuvette or the like, the reaction zone and the detection zone typically refer to the same fluid containing portion of the receptacle. For example, within the fluid containing portion of a cuvette, reagents are mixed, reacted and subsequently detected. Typically, in order to expedite the process of performing assays, e.g., screening assays, multiplexed receptacles are optionally used. Examples of such receptacles include, e.g., multiwell plates, e.g., 96-well, 384-well or 1536-well plates.

For capillary or channel based aspects, the reaction zone and the detection zone optionally comprise the same fluid-containing portion of the receptacle. However, in many aspects, the reaction zone and the detection zone are separate fluid containing portions of the receptacle. Specifically, reagents are optionally mixed and reacted in one portion of the receptacle, and subsequently moved to a separate detection zone whereupon the reaction products, etc. are detected.

In particularly preferred aspects, the container comprises a microfluidic device. As used herein, the term "microfluidic device" refers to a device or body structure which includes and/or contains at least one fluidic component, e.g., a channel, chamber, well or the like, which has at least one cross sectional dimension that is between about 0.1 and about 500 $\mu$m, with these channels and/or chambers often having at least one cross-sectional dimension between about 0.1 $\mu$m and 200 $\mu$m, in some cases between about 0.1 $\mu$m and 100 $\mu$m, and often between about 0.1 $\mu$m and 20 $\mu$m. Such cross-sectional dimensions include, e.g., width, depth, height, diameter or the like. Typically, structures having these dimensions are also described as being "microscale." Microfluidic devices in accordance with the present invention, typically include at least one, and generally more than one channel and/or chamber disposed within a single body structure. Such channels/chambers are optionally separate and discrete, or alternatively, they are optionally fluidly connected. Such fluid connections are optionally provided by channels, channel intersections, valves and the like. Channel intersections optionally exist in a number of formats, including cross intersections, "T" intersections, or any number of other structures whereby two channels are in fluid communication.

The body structure of the microfluidic devices described herein typically comprises an aggregation of two or more separate components which, when appropriately mated or joined together, form the microfluidic device of the invention, e.g., containing the channels and/or chambers described herein. Typically, the microfluidic devices described herein are fabricated as an aggregate of substrate layers. In particular, such preferred devices comprise a top portion, a bottom portion, and an interior portion, wherein the interior portion substantially defines the channels and chambers of the device.

Figure 6:
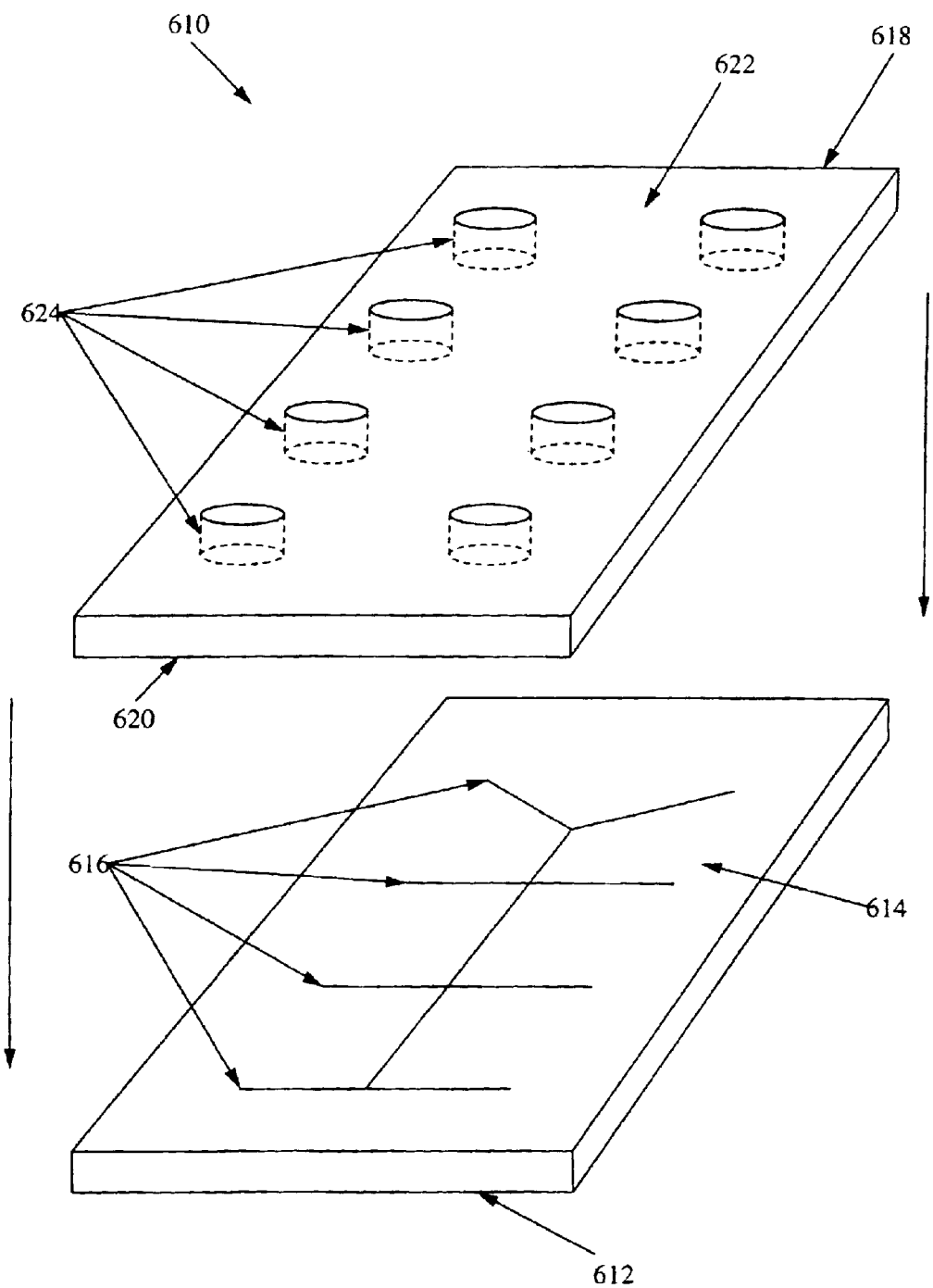
FIG. 6 is a schematic illustration of a multi-layered microfluidic device that is optionally employed as a reaction/assay receptacle in the present invention.

FIG. 6 illustrates two-layer body structure 610, for a microfluidic device. In preferred aspects, bottom portion 612 of the device comprises a solid substrate that is substantially planar in structure, and which has at least one substantially flat upper surface 614. A variety of substrate materials are optionally employed as the bottom portion. Typically, because the devices are microfabricated, substrate materials are selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices are optionally exposed, including extremes of pH, temperature, salt concentration, and application of electric fields. Accordingly, in some preferred aspects, the substrate material can include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), and the like. Such polymeric substrates are readily manufactured using available microfabrication techniques, as described above, or from microfabricated masters, using well known molding techniques, such as injection molding, embossing or stamping or the like. Such polymeric substrate materials are preferred for their ease of manufacture, low cost and disposability, as well as their general inertness to most extreme reaction conditions. Again, these polymeric materials optionally include treated surfaces, e.g., derivatized or coated surfaces, to enhance their utility in the microfluidic system, e.g., provide enhanced fluid direction, e.g., as described in U.S. Pat. No. 5,885,470, which is incorporated herein by reference in its entirety for all purposes.

The channels and/or chambers of the microfluidic devices are typically fabricated into the upper surface of the bottom substrate or portion 612 (although they are optionally fabricated into either or both of the upper surface of the bottom substrate or the lower surface of the upper substrate) as microscale grooves or indentations 616, using the above described microfabrication techniques. The top portion or substrate 618 also comprises first planar surface 620, and second surface 622 opposite first planar surface 620. In the microfluidic devices prepared in accordance with the methods described herein, the top portion also includes a plurality of apertures, holes or ports 624 disposed therethrough, e.g., from first planar surface 620 to second surface 622 opposite the first planar surface.

First planar surface 620 of top substrate 618 is then mated, e.g., placed into contact with, and bonded to planar surface 614 of bottom substrate 612, covering and sealing the grooves and/or indentations 616 in the surface of the bottom substrate, to form the channels and/or chambers (i.e., the interior portion) of the device at the interface of these two components. Holes 624 in the top portion of the device are oriented such that they are in communication with at least one of the channels and/or chambers formed in the interior portion of the device from the grooves or indentations in the bottom substrate. In the completed device, these holes function as reservoirs for facilitating fluid or material introduction into the channels or chambers of the interior portion of the device, as well as providing ports at which electrodes or pressure control elements are optionally placed into contact with fluids within the device, allowing application of electric fields along the channels of the device to control and direct fluid transport within the device.

In many embodiments, the microfluidic devices include an optical detection window disposed across one or more channels and/or chambers of the device, permitting FP detection by a proximal detector. Optical detection windows are typically transparent such that they are capable of transmitting an optical signal from the channel/chamber over which they are disposed. Optical detection windows are optionally merely a region of a transparent cover layer, e.g., where the cover layer is glass or quartz, or a transparent polymer material, e.g., PMMA, polycarbonate, etc. Alternatively, where opaque substrates are used in manufacturing the devices, transparent detection windows fabricated from the above materials are optionally separately manufactured into the device.

Figure 7:
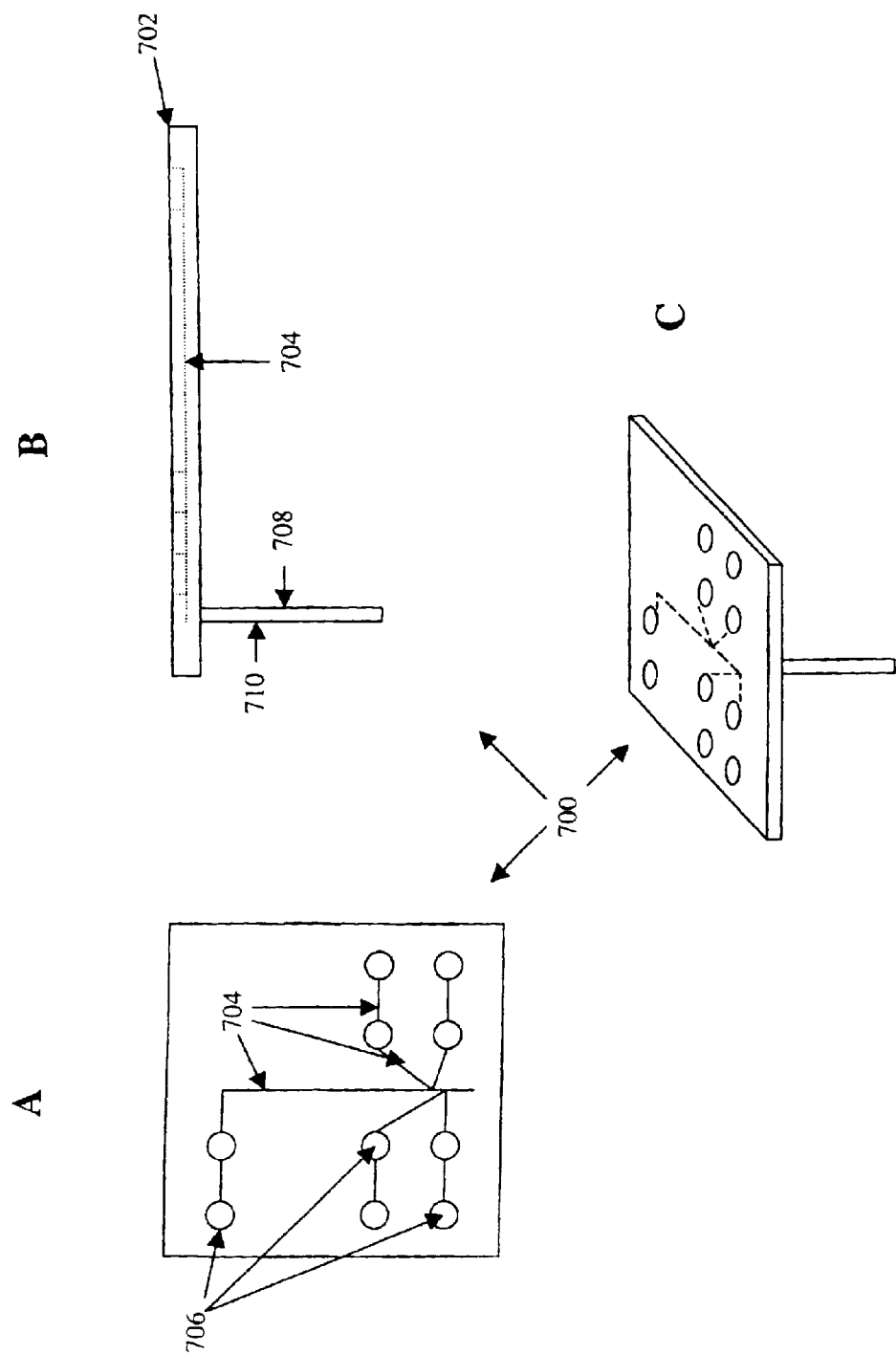
FIG. 7, Panels A–C, is a schematic illustration of a microfluidic device incorporating an external sampling pipettor as a reaction/assay receptacle in the present invention.

As described in greater detail below, these devices are optionally used in a variety of applications, including, e.g., the performance of high throughput screening assays in drug discovery, immunoassays, diagnostics, genetic analysis, and the like. As such, the devices described herein, will often include multiple sample introduction ports or reservoirs, for the parallel or serial introduction and analysis of multiple samples. Alternatively, these devices are optionally coupled to a sample introduction port, e.g., a pipettor, which serially introduces multiple samples into the device for analysis. Examples of such sample introduction systems are described in e.g., U.S. Pat. No. 5,779,868 and published International Patent Application Nos. WO 98/00705 and WO 98/00231, each of which is incorporated herein by reference in its entirety for all purposes. A schematic illustration of a microfluidic device incorporating an external sample pipettor is illustrated in FIG. 7, described below.

In the case of some substrates, e.g., glass, quartz, or silica, it is sometimes desirable to include a coating material in the channels of the microfluidic device. This is primarily to reduce the level of interaction between the components of the hybridization assay and the charged surface of the substrate. Any of a variety of known coating materials are useful in this regard, including polymer coatings typically used in electrophoretic applications, e.g., linear polyacrylamides, e.g., polydimethylacrylamides (PDMA), and the like (see, e.g., U.S. Pat. Nos. 5,948,227, 5,567,292, and 5,264,101, each of which is incorporated by reference). Such polymers can be silica adsorbing, or can be covalently attached to the surface of the substrates, e.g., through the inclusion of an epoxide group on the polymer chain (see, e.g., Chiari et al., HPCE Conference, March, 2000), in order to mask surface charges on the substrate which can interact with the species in the reaction mixture.

In one aspect, nucleic acids or other components relevant to an FP assay of the invention are introduced into the microfluidic device from an external source. Briefly, in one embodiment, microfluidic device 700, e.g., similar to that described with reference to FIG. 6, is provided having body structure 702 which includes network of internal channels 704 that are connected to series of reservoirs 706 disposed in the body structure 702. The various reservoirs are used to introduce various reagents into channels 704 of the device. Capillary element 708 is coupled to the body structure 702, such that channel 710 that is disposed within and runs the length of capillary element 708 is fluidly connected to channel network 704 in the body structure. This capillary element is then used to draw up a variety of different sample or test materials, in series, for analysis within the device.

As described above, the methods and systems of the present invention typically rely upon a change in the level of fluorescence polarization of a reaction mixture as a result of the reaction of interest (e.g., hybridizing nucleic acids). As such, an appropriate detection system is typically utilized to differentiate, or quantify polarized from depolarized emitted fluorescence. Generally speaking, such a detection system typically separately detects fluorescent emissions that are emitted in the same plane of the polarized excitation light, and fluorescent emissions emitted in a plane other than the plane of the excitation light.

Figure 8:
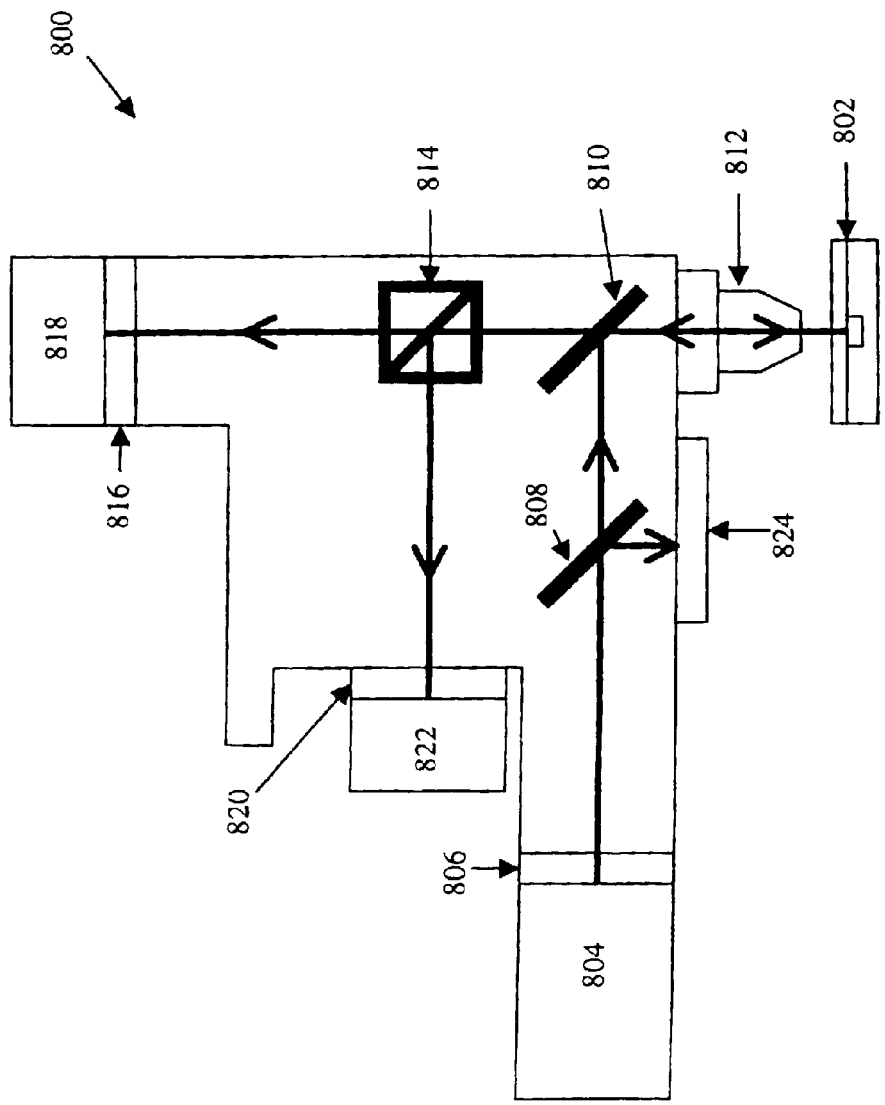
FIG. 8 is a schematic illustration of one example of an optical detection system for use with the present invention.

One example of an FP detection system is shown in FIG. 8. As shown, the fluorescence polarization detector includes light source 804, which generates light at an appropriate excitation wavelength for the fluorescent compounds that are present in the assay system. Typically, coherent light sources, such as lasers, laser diodes, and the like are preferred because of the highly polarized nature of the light produced thereby. The excitation light is directed through optional polarizing filter 806, which passes only light in one plane, e.g., polarized light. The polarized excitation light is then directed through an optical train, e.g., dichroic mirror 810 and microscope objective 812 (and optionally, reference beam splitter 808), which focuses the polarized light onto the sample receptacle (illustrated as a channel in microfluidic device 802), in which the sample to be assayed is disposed.

Fluorescence emitted from the sample is then collected, e.g., through objective 812, and directed back through dichroic mirror 810, which passes the emitted fluorescence and reflects the reflected excitation light, thereby separating the two. The emitted fluorescence is then directed through beam splitter 814 where one portion of the fluorescence is directed through filter 816 that filters out fluorescence that is in the plane that is parallel to the plane of the excitation light and directs the perpendicular fluorescence onto first light detector 818. The other portion of the fluorescence is passed through filter 820 that filters out the fluorescence that is perpendicular to the plane of the excitation light, directing the parallel fluorescence onto second light detector 822. In alternative aspects, beam splitter 814 is substituted with a polarizing beam splitter, e.g., a Glan prism, obviating the need for filters 816 and 820. These detectors 818 and 822 are then typically coupled to an appropriate recorder or processor (not shown in FIG. 8) where the light signal is recorded and or processed as set out in greater detail below. Photomultiplier tubes (PMTs), are generally preferred as light detectors for the quantification of the light levels, but other light detectors are optionally used, such as photodiodes, or the like.

The detector is typically coupled to a computer or other processor, which receives the data from the light detectors, and includes appropriate programming to compare the values from individual detectors to determine the amount of polarization from the sample. In particular, the computer typically includes software programming which receives as input the fluorescent intensities from each of the different detectors, e.g., for parallel and perpendicular fluorescence. The fluorescence intensity is then compared for each of the detectors to yield a fluorescence polarization value. One example of such a comparison is given by the equation:

$$P = [I(\|) - I(\perp)] / [I(\|) + I(\perp)] C \quad (4)$$

as shown above, except including a correction factor (C), which corrects for polarization bias of the detecting instrument. The computer determines the fluorescence polarization value for the reaction of interest. From that polarization value and based upon the polarization values for free and bound fluorescence, the computer calculates the ratio of bound to free fluorescence. Alternatively, the polarization values pre and post reaction are compared and a polarization difference (ΔP) is determined. The calculated polarization differences can then be used as absolute values, e.g., to identify potential effectors of a particular reaction, or they can be compared to polarization differences obtained in the presence of known inhibitors or enhancers of the reaction of interest, in order to quantify the level of inhibition or enhancement of the reaction of interest by a particular compound.

Figure 9:
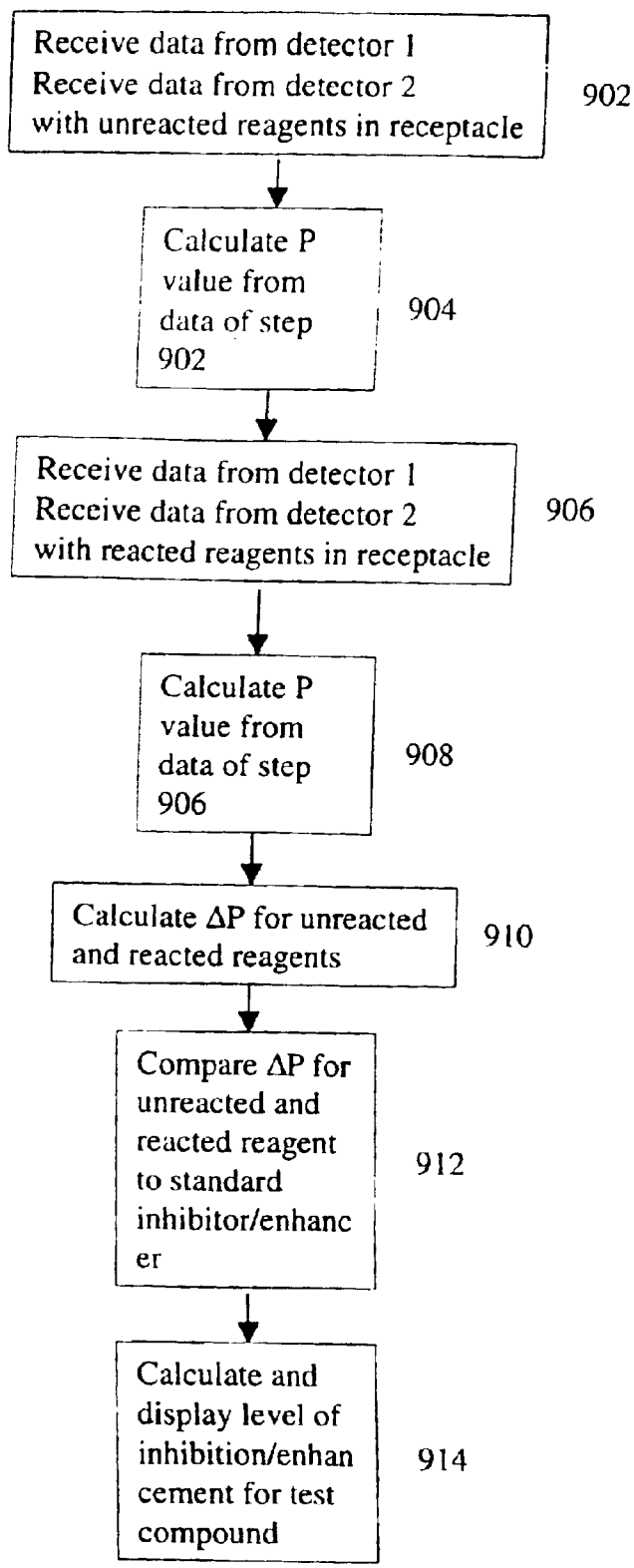
FIG. 9 is a flow chart of a software program or computer implemented process carried out by an assay system in performing the assays of the present invention.

FIG. 9 illustrates a flow-chart for the processes carried out by the computer using the above-described software programming. As shown, the programmed process begins at step 902 where the computer receives the fluorescence intensity data for the unreacted reagents (i.e., unhybridized nucleic acids) in the reaction zone (e.g. in receptacle 502 of FIG. 5) from the two detectors, e.g., detectors 818 and 820 of FIG. 8. The fluorescence polarization value (P) is then calculated in step 904, e.g., according to the equations described herein. At step 906, the computer receives fluorescence intensity data for the reacted reagents (e.g., nucleic acids) from the two detectors. Again, at step 908, the P value is calculated for the reacted reagents. At step 910, the P values for the reacted and unreacted reagents are compared, e.g., one is subtracted from the other to yield a ΔP value for the reaction. At this point, the ΔP value can be displayed as a measure of the reaction, e.g., its rate or completeness.

Optionally, the ΔP value can be compared to a standard ΔP value, i.e., from a reaction having a known rate, level of inhibition or enhancement, e.g., at step 912. Through this comparison, the computer optionally then interpolates or extrapolates a quantitative measure of the reaction, its level of inhibition or enhancement which quantitative measurement can then be displayed to the investigator, e.g., at step 914. As noted above, the computer optionally includes a determined polarization value for completely free and completely bound fluorescence. In that case, determination of fluorescence differences is not necessary, thus permitting the omission of several steps of the program. In that case, the computer receives the fluorescence data from the detector for the reacted mixture. The computer then merely calculates the P value for the reaction mixture and determines the ratio of bound fluorescence to free fluorescence (e.g., in accordance with equation (3), supra). The ratio is then used to quantitate the reaction.

In the case of high-throughput screening assay systems, the computer software optionally instructs the correlation of a particular screened result to a particular sample or sample acquisition location. This permits the investigator to identify the particular reagents employed in any one assay.

Figure 10A:
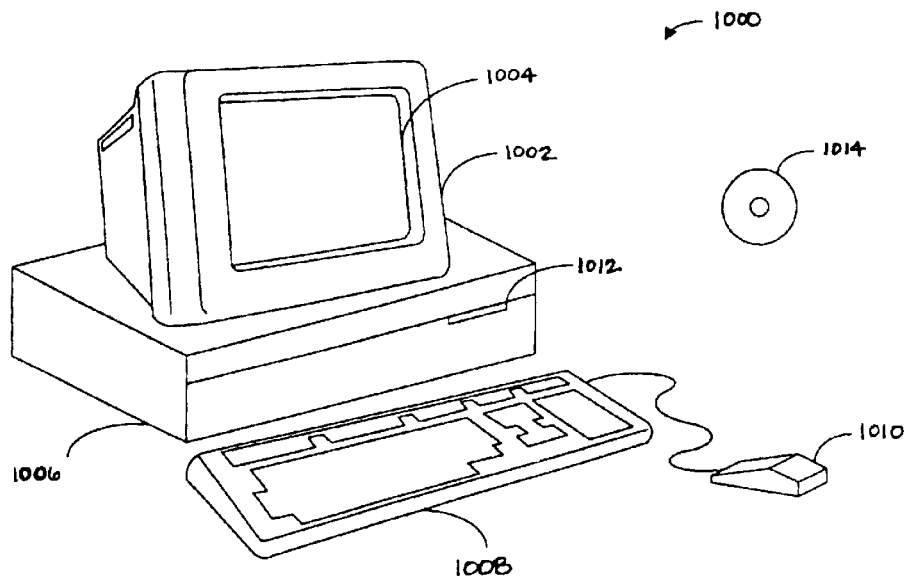
FIGS. 10A–B illustrate an exemplary computer system and architecture for use with the present invention.
Figure 10B:
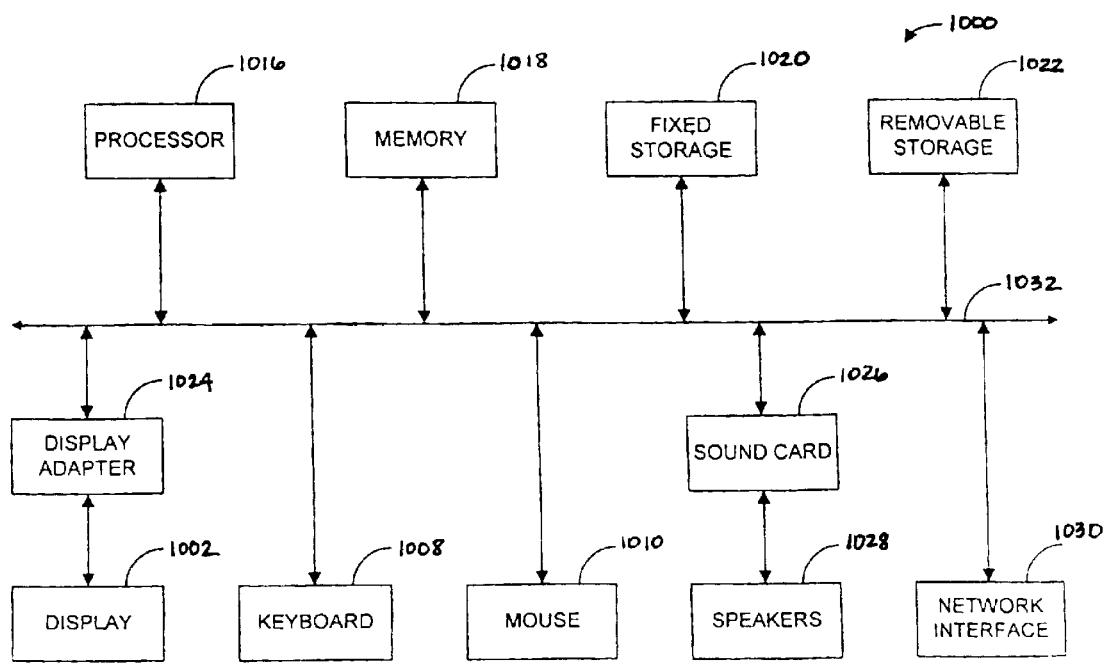

FIG. 10 schematically illustrates a computer and architecture typically used in accordance with the present invention. In particular, FIG. 10A illustrates an example of a computer system that can be used to execute software for use in practicing the methods of the invention or in conjunction with the devices and/or systems of the invention. Computer system 1000 typically includes a display 1002, screen 1004, cabinet 1006, keyboard 1008, and mouse 1010. Mouse 1010 can have one or more buttons for interacting with a graphic user interface (GUI). Cabinet 1006 typically houses a CD-ROM drive 1012, system memory and a hard drive (see FIG. 10B) which are optionally utilized to store and retrieve software programs incorporating computer code that implements the methods of the invention (e.g., by performing FP calculations) and/or controls the operation of the devices and systems of the invention, data for use with the invention, and the like. Although CD-ROM 1014 is shown as an exemplary computer readable storage medium, other computer readable storage media, including floppy disk, tape, flash memory, system memory, and hard drive(s) can, of course be substituted (or used in combination). Additionally, a data signal embodied in a carrier wave (e.g., in a network, e.g., internet, intranet, and the like) can be or comprise the computer readable storage medium.

FIG. 10B schematically illustrates a block diagram of the computer system 1000, described above. As in FIG. 10A, computer system 1000 includes monitor or display 1002 (e.g., for displaying FP measurement data), keyboard 1008, and mouse 1010. Computer system 1000 also typically includes subsystems such as a central processor 1016 (e.g., capable of running software for FP calculation), system memory 1018, fixed storage 1020 (e.g., hard drive) removable storage 1022 (e.g., CD-ROM drive) display adapter 1024, sound card 1026, speakers 1028 and network interface 1030. Other computer systems available for use with the invention can include fewer or additional subsystems. For example, another computer system optionally includes more than one processor 1014.

The system bus architecture of computer system 1000 is illustrated by arrows 1032. However, these arrows are illustrative of any interconnection scheme serving to link the subsystems. For example, a local bus could be utilized to connect the central processor to the system memory and display adapter. Computer system 1000 shown in FIG. 10A is but an example of a computer system suitable for use with the invention. Other computer architectures having different configurations of subsystems are optionally utilized, including embedded systems, such as on-board processors on the controller detector instrumentation, and "internet appliance" architectures, where the system is connected to the main processor via an internet hook-up.

The computer system typically includes appropriate software for receiving user instructions, either in the form of user input into set parameter fields, e.g., in a GUI, or in the form of preprogrammed instructions, e.g., preprogrammed for a variety of different specific operations (e.g., related to FP measurement, or related calculations). The software then converts these instructions to appropriate language for instructing the operation of the optional material transport system, and/or for controlling, manipulating, storing etc., the data received from the detection system. In particular, the computer typically receives the data from the detector (e.g., relating to FP measurements), interprets the data, and either provides it in one or more user understood or convenient formats, e.g., plots of raw data, calculated dose response curves, hybridization constants, and the like, or uses the data to initiate further controller instructions in accordance with the programming, e.g., controlling flow rates, applied temperatures, reagent concentrations, etc.

As described above, the present invention is optionally carried out in a microfluidic device or system. As such, it is generally desirable to provide a means or system for moving materials through, between and among the various channels, chambers and zones that are contained in such devices. A variety of material transport methods are optionally used in accordance with such microfluidic devices. For example, in one preferred aspect, material movement through the channels of a device is caused by the application of pressure differentials across the channels through which material flow is desired. This can be accomplished by applying a positive pressure to one end of a channel or a negative pressure to the other end. In complex channel networks, controlled flow rates in all of the various interconnected channels can be controlled by the inclusion of valves, and the like within the device structure, e.g., to stop and start flow through a given channel. Alternatively, channel resistances can be adjusted to dictate the rate, timing and/or volume of material movement through different channels, even under a single applied pressure differential, e.g., a vacuum applied at a single channel port. Examples of such channel networks are illustrated in e.g., U.S. patent application Ser. No. 09/238,467, filed Jan. 28, 1999, and Ser. No. 09/233,700, filed Jan. 19, 1999 and Ser. No. 09/277,367, filed Mar. 26, 1999, all of which are hereby incorporated herein by reference in their entirety for all purposes.

Alternately, for microfluidic applications of the present invention, controlled electrokinetic transport systems can be used. This type of electrokinetic transport is described in detail in U.S. Pat. No. 5,858,195, to Ramsey, which is incorporated herein by reference for all purposes. Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel, will cause the proton sheath to move in the direction of the voltage drop, i.e., toward the negative electrode.

"Controlled electrokinetic material transport and direction," as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage). However, this type of material flow through the intersection would result in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection can then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves which include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the 'off' mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed in this manner. Although described for the purposes of illustration with respect to a four way, cross intersection, these controlled electrokinetic material transport systems can be readily adapted for more complex interconnected channel networks, e.g., arrays of interconnected parallel channels.

Figure 11:
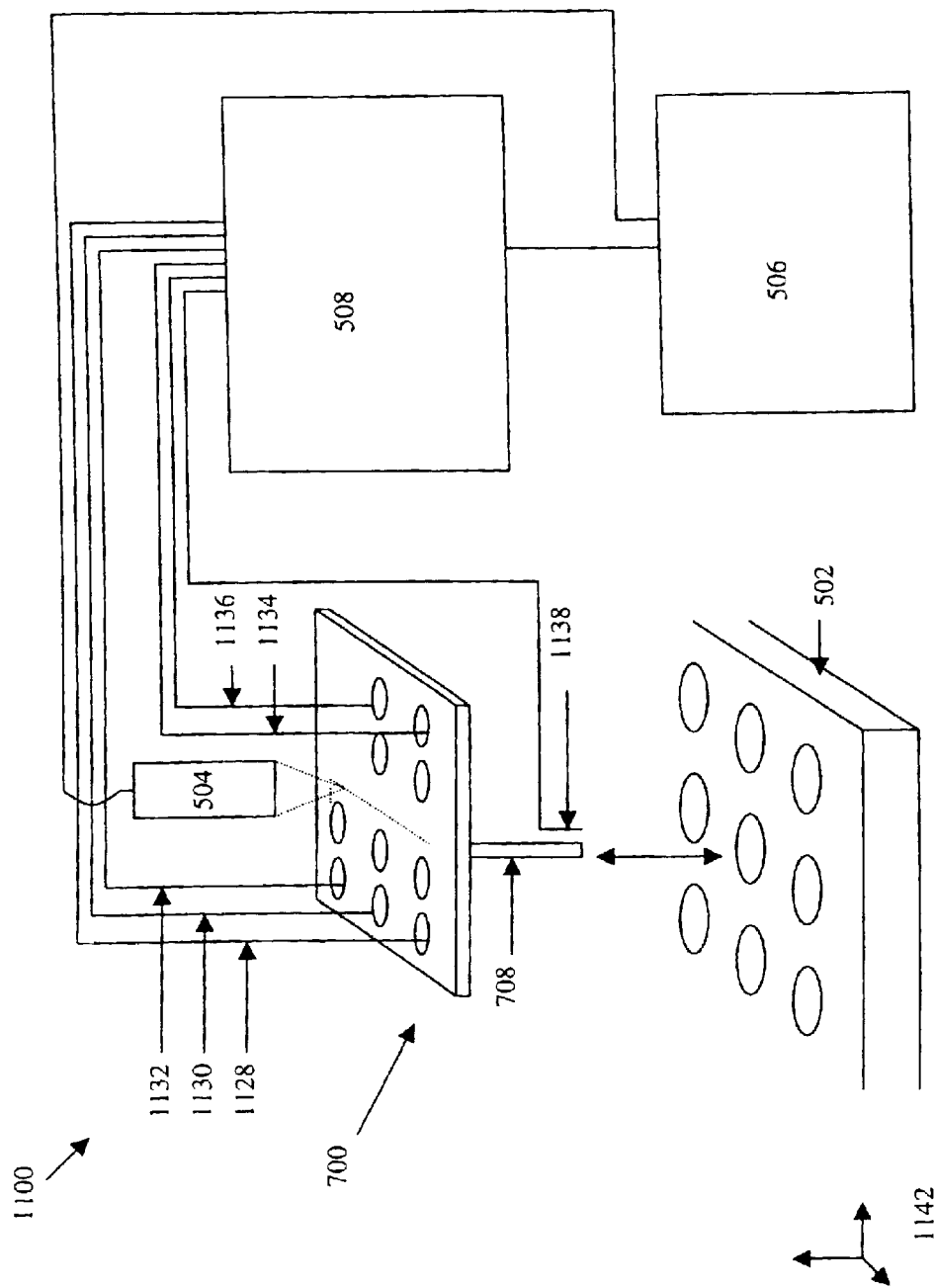
FIG. 11 illustrates the interfacing of a microfluidic device with other elements of a system for controlling material movement, detecting assay results from the microfluidic device, and analyzing those results.
Figure 12:
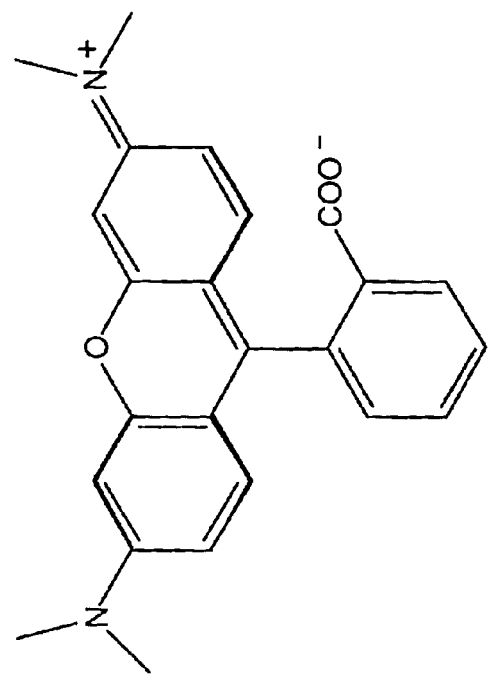
FIG. 12 shows example structures for Fluorescein and Rhodamine. Rhodamine labeled PNA probes do not require the addition of poly-lysine to amplify the FP signal.
Figure 12:
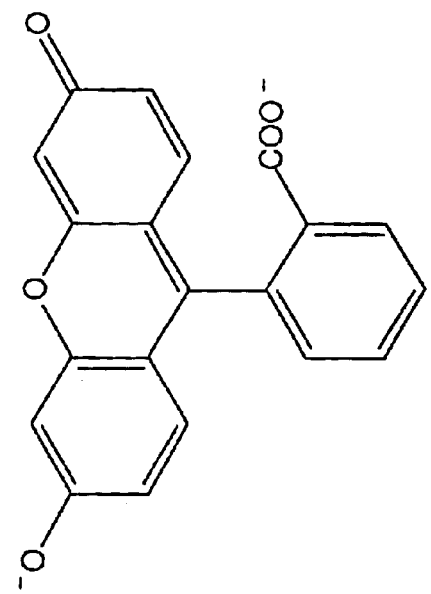

An example of a system employing this type of electrokinetic transport system in a microfluidic device, e.g., as illustrated in FIG. 7, is shown in FIG. 11. As shown, the system 1100 includes microfluidic device 700, which incorporates integrated pipettor/capillary element 708. Each of electrical access reservoirs 706, has a separate electrode (1128–1136) disposed therein, e.g., contacting the fluid in the reservoirs. Each of electrodes 1128–1136 is operably coupled to electrical controller 508 that is capable of delivering multiple different voltages and/or currents through the various electrodes. Additional electrode 1138, also operably coupled to controller 1108, is positioned so as to be placed in electrical contact with the material that is to be sampled, e.g., in multiwell plate 502, when capillary element 708 is dipped into the material. For example, electrode 1138 is optionally an electrically conductive coating applied over capillary 708 and connected to an electrical lead which is operably coupled to controller 508. Alternatively, electrode 1138 can simply include an electrode wire positioned adjacent the capillary so that it will be immersed in/contacted with the sample material along with the end of the capillary element 708. Alternatively, the electrode can be associated with the source of material, as a conductive coating on the material source well or as a conductive material from which the source well was fabricated. Establishing an electric field then simply operates by contacting the electrical lead with the source well material or coating. Additional materials are sampled from different wells on the multiwell plate 502, by moving one or more of the plate 502 and/or device 700 relative to each other prior to immersing the pipettor 1138 into a well. Such movement is typically accomplished by placing one or more of the device 700 or multiwell plate 502 on a translation stage, e.g., the schematically illustrated x-y-z translation stage 1142.

In still a further optional application, hybrid material transport methods and systems can be employed. Briefly, one embodiment of such hybrid systems relies upon the use of electrokinetic forces to generate pressure differentials within microfluidic systems. Such hybrid systems combine the controllability of electrokinetic systems with the advantages of pressure based systems, e.g., lack of electrophoretic biasing effects. Such hybrid systems are described in, e.g., Published International Patent Application No. WO 99/16162, which is incorporated herein by reference in its entirety for all purposes. Other hybrid systems optionally employ electrokinetic forces to move materials in one portion of the channel network, while employing pressure based forces in other portions of the channel network.

A variety of other systems can be employed in practicing the present invention including without limitation, e.g., rotor systems, dipstick systems, spotted array systems and the like.

Kits and Reagents

The reagents for carrying out the methods and assays of the present invention are optionally provided in a kit form to facilitate the application of these assays for the user. Such kits also typically include instructions for carrying out the subject assay, and optionally include the fluid receptacle, e.g., the cuvette, multiwell plate, microfluidic device, etc. in which the reaction is to be carried out.

Typically, reagents included within the kit include a probe that bears a positive or neutral fluorescent label and optionally further includes one or more target or control nucleic acid. These reagents are optionally provided in vials for measurement by the user, or in pre-measured vials, ampoules or microfluidic devices. The reagents are simply combined to yield an appropriate hybridization mixture, e.g., optionally with one or more target nucleic acid provided by the user. The reagents are optionally provided in liquid and/or lyophilized form and optionally include appropriate buffer solutions for dilution and/or rehydration of the reagents. Typically, all of the reagents and instructions are co-packaged in a single box, pouch or the like that is ready for use.

EXAMPLES

The following examples are illustrative and not limiting. One of skill will recognize a variety of non-critical parameters can be altered without materially affecting the results obtained.

Example Detection of PNA/DNA Hybridization

This example provides a demonstration that accurate FP measurements can be made for rhodamine-labeled PNAs, even in the absence of an FP enhancer such as polylysine.

FIG. 1 is a schematic representation of DNAs and PNAs. The top panel is a schematic of a single stranded DNA. The middle panel is a schematic of a single-stranded PNA. The bottom panel is a schematic overlay of the DNA and PNA, showing the similarity of the overall structure of the two molecules.

As noted herein, PNAs have the advantage, when used as probes, of good sensitivity for SNP detection (i.e., due to large $T_m$ differences). In addition, PNAs have high affinity for DNA, providing fast PNA-DNA hybridization kinetics. PNAs are also nuclease resistant and have a neutral backbone. PNA-DNA hybridization detection is relevant in a number of contexts, including assays based on mobility shift analysis, electrochemical approaches, mono-clonal anti-(PNA/DNA hybrid) antibodies, MALDI-TOF MS of PNA/DNA hybrids, use of PNA-based molecular beacons and in various FRET-based approaches. LNAs have many of the same advantages and can also similarly be used in the methods, compositions, systems, devices and kits of the invention.

As shown in FIG. 2A, previous methods for FP detection of nucleic acid hybridization have utilized, e.g., polylysine to improve FP differences (e.g., to improve the dynamic range of FP dependent assays). DNA/DNA hybrids have been detected by fluorescence polarization before, but the observed changes in FP were quite low (10–30 mP). DNA binding proteins (e.g., mutant versions of EcoRI) have also been used in the past for increasing the dynamic range of the assays. Biotinylated, dye-labeled DNA/DNA hybrids have been detected by fluorescence polarization in the presence of streptavidin.

As noted in more detail above, FP depends on molecular size. For example, $P=(Ivv-Ivh)/(Ivv+Ivh)$, where P is the measured fluorescence polarization and Ivv and Ivh are intensities of the emitted light in planes parallel (vv) and perpendicular (vh) to the plane of the excitation light. As specified by the Perrin equation, $(1IP-1/3)=(1/P_0-1/3)(1-3\tau/\rho)$ where $\rho$ is the rotational relaxation time for a sphere; $\tau$ is the fluorescence decay time and P and $P_0$ are the measured and the so-called limiting polarization value. The rotational relaxation time is related to the volume of the molecule: $3\eta V/RT$, as noted above (Equation 1). FIG. 2A provides an illustration of FP as a function of molecular size, i.e., in the presence of polylysine.

FIG. 2B shows a summary of hybridization data with three PNAs. "PLL" indicates that the FP measurement was conducted in the presence of polylysine.

Figure 2:
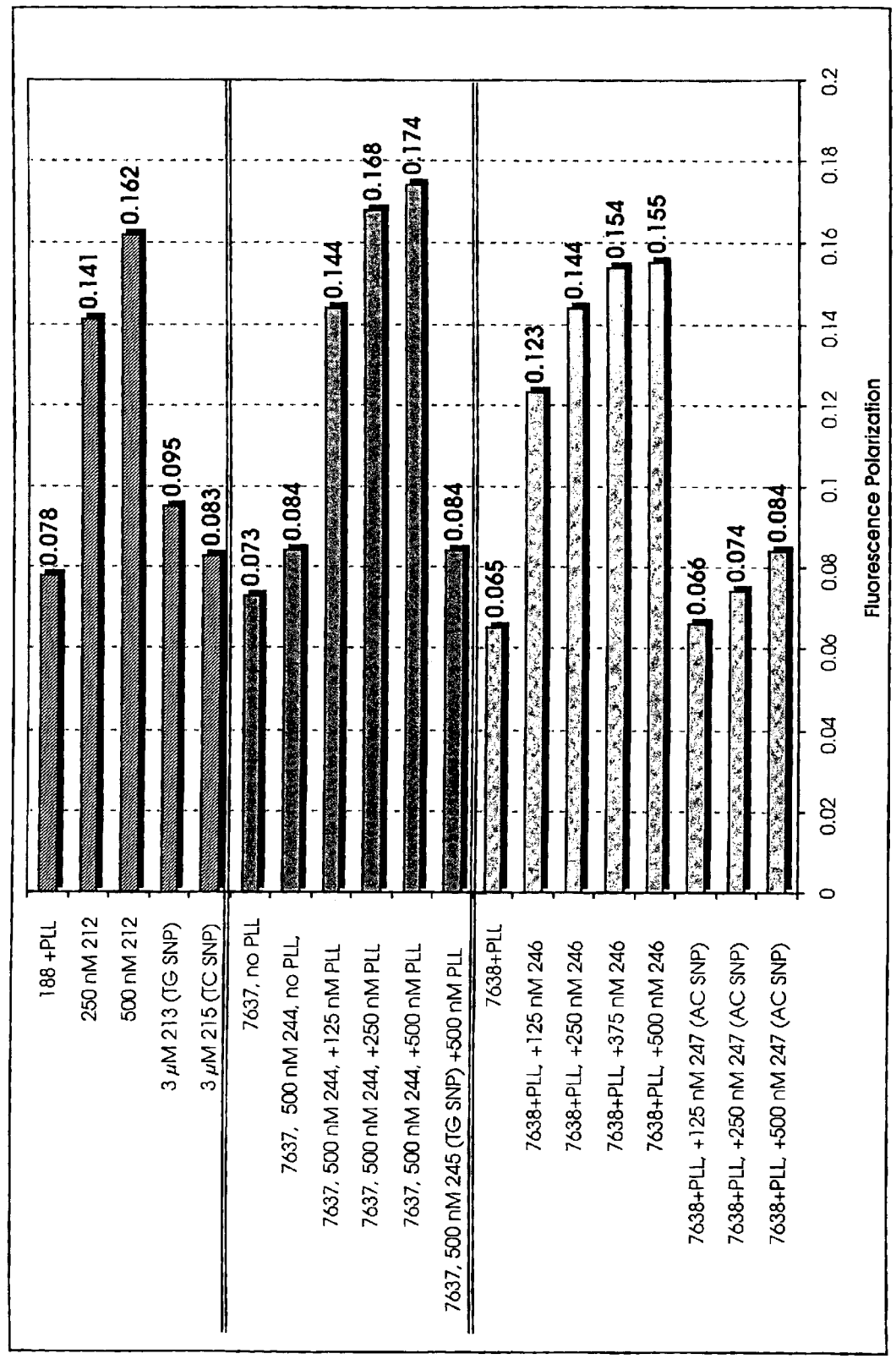
FIG. 2A schematically shows the use of poly-lysine for PNA-DNA hybrid detection.
FIG. 2B shows several histograms summarizing hybridization data for three PNAs.
FIG. 2C shows a histogram depicting the kinetics of PNA/DNA hybridization as detected by FP in the presence of polylysine (see also, Anal. Biochem. 275, 248 (1999)).
FIG. 2D shows several melting curves analyzed by FP.
FIG. 2E shows graphs depicting the effects of mismatch position on PNA/DNA duplex stability with PNA probe 188 (a 9-mer). Assay conditions were: 50 nM PNA 188, 50 mM HEPES pH 7.5, 3.3 $\mu$M Poly L-Lysine.
Figure 2C:
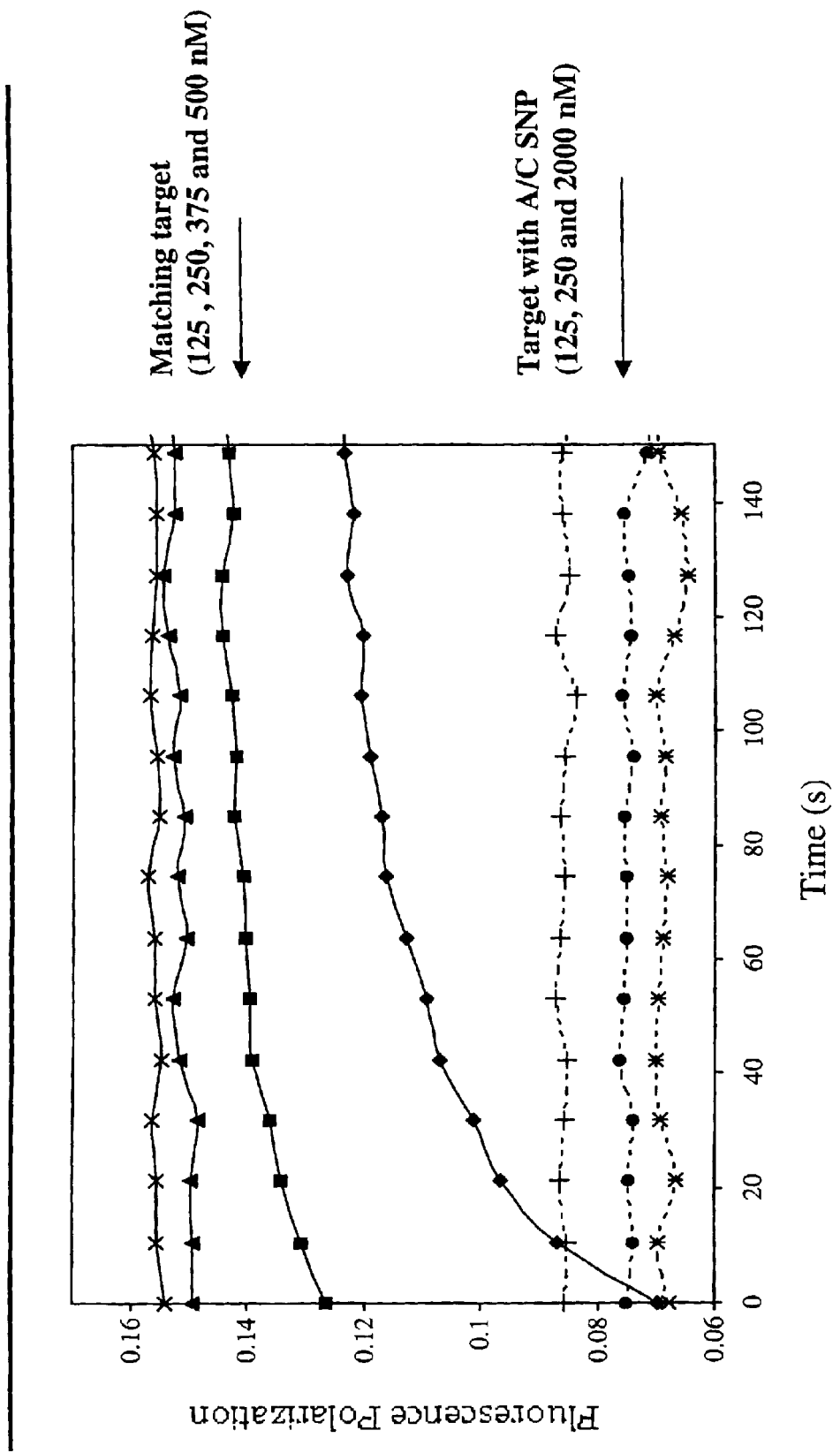
Figure 2D:
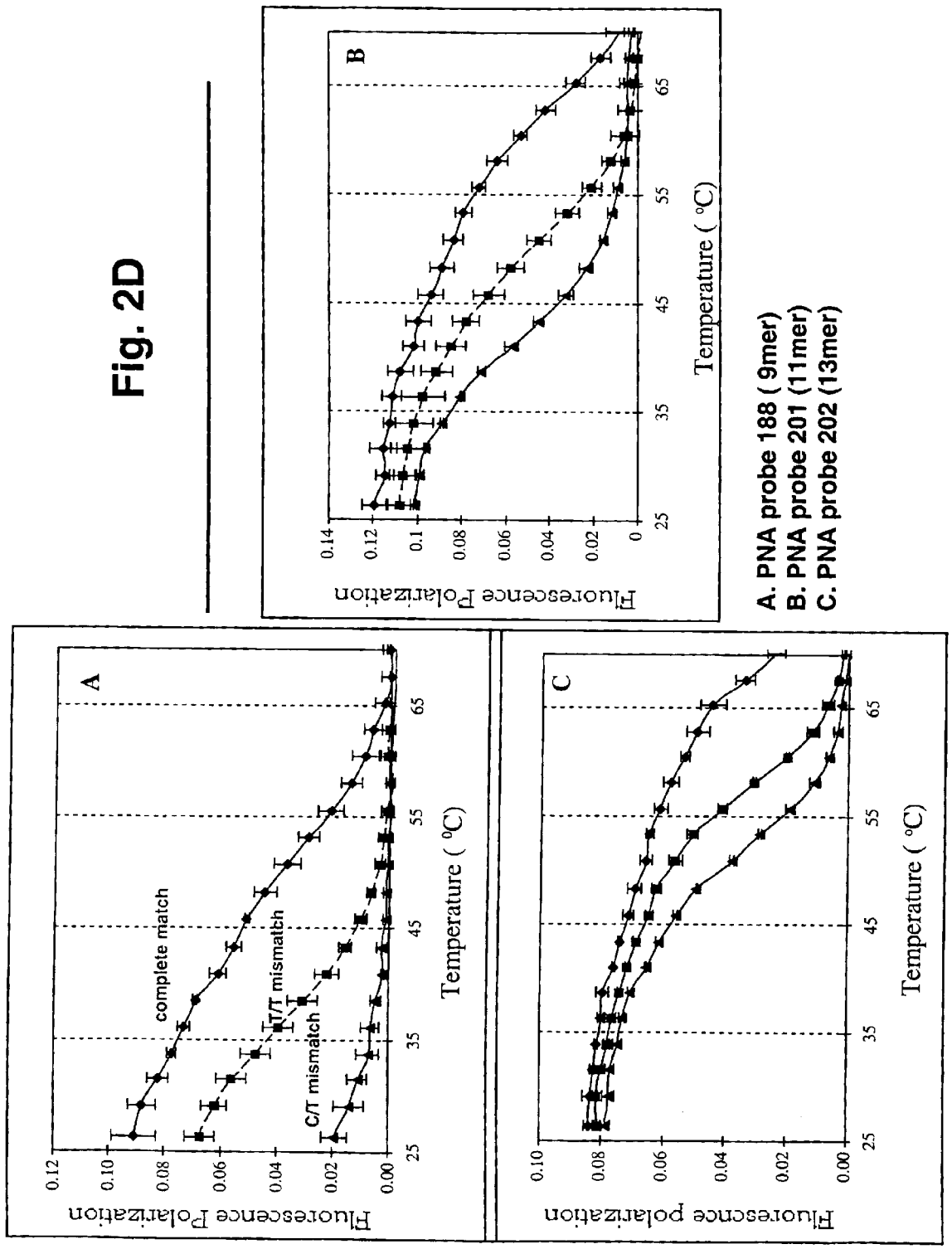
Figure 2E:
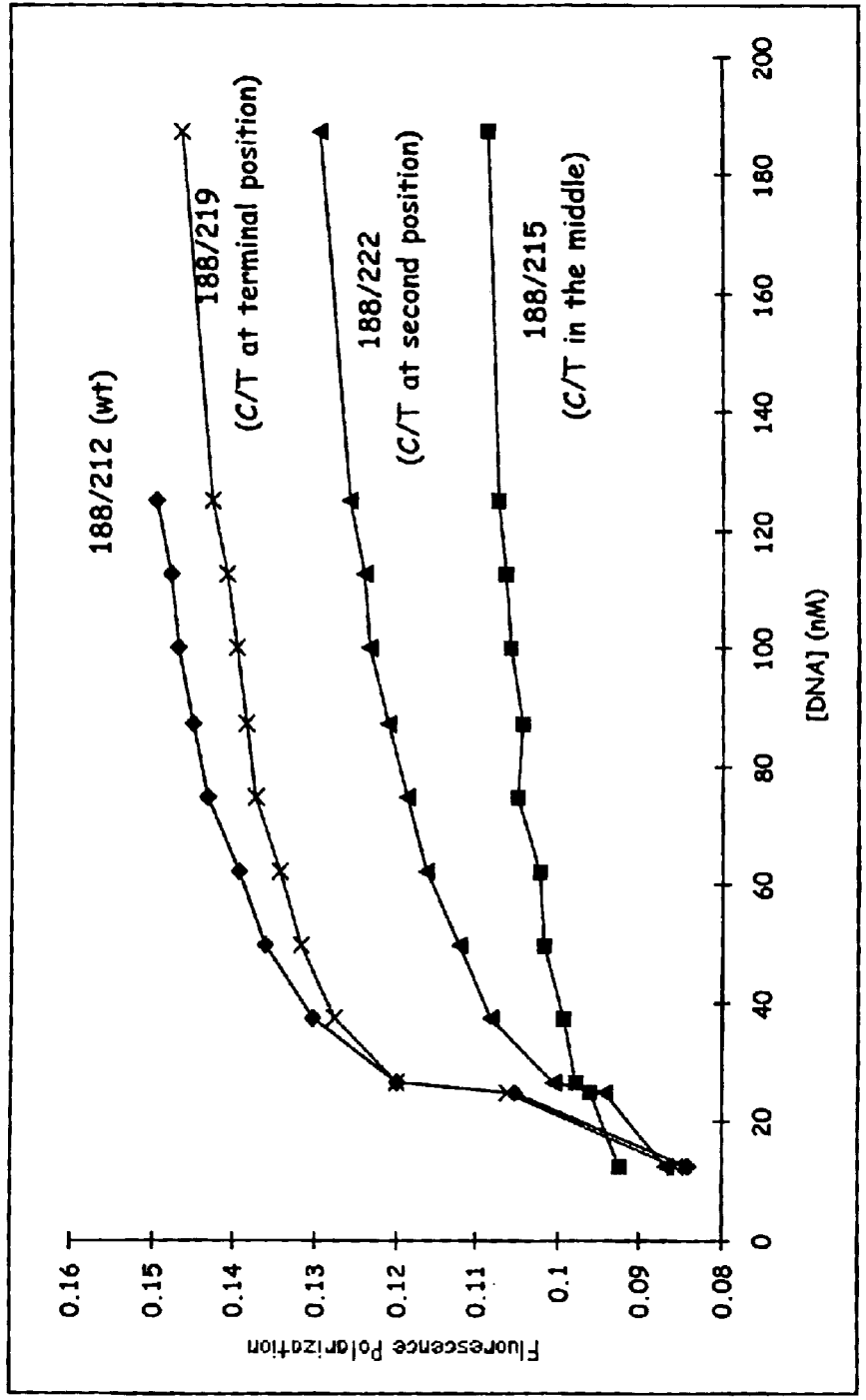
Figure 3A:
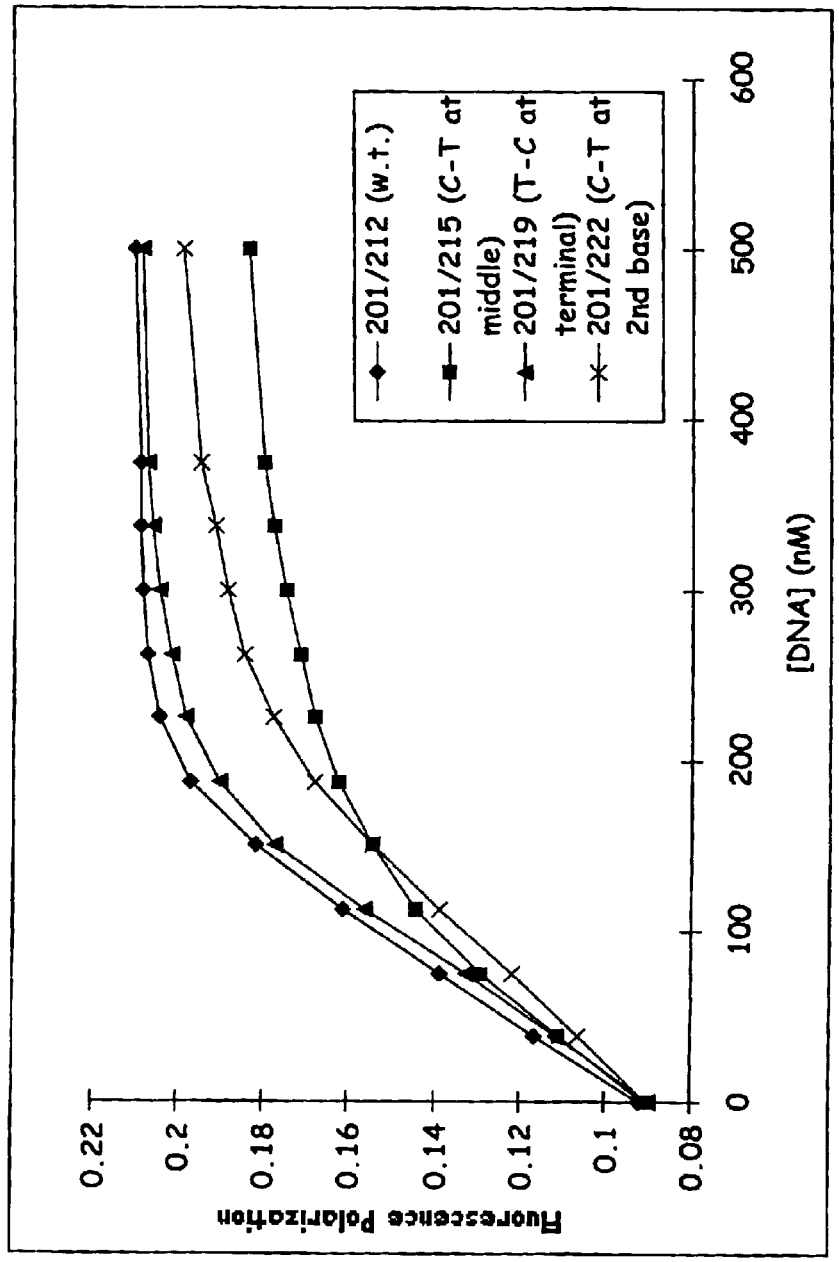
FIG. 3A depicts a graph showing the effects of mismatch position on PNA/DNA duplex stability for PNA probe 201 (an 11-mer). Assay conditions included: 50 nM PNA 201, 50 mM HEPES pH 7.5, 3.3 $\mu$M Poly L-Lysine.
Figure 3B:
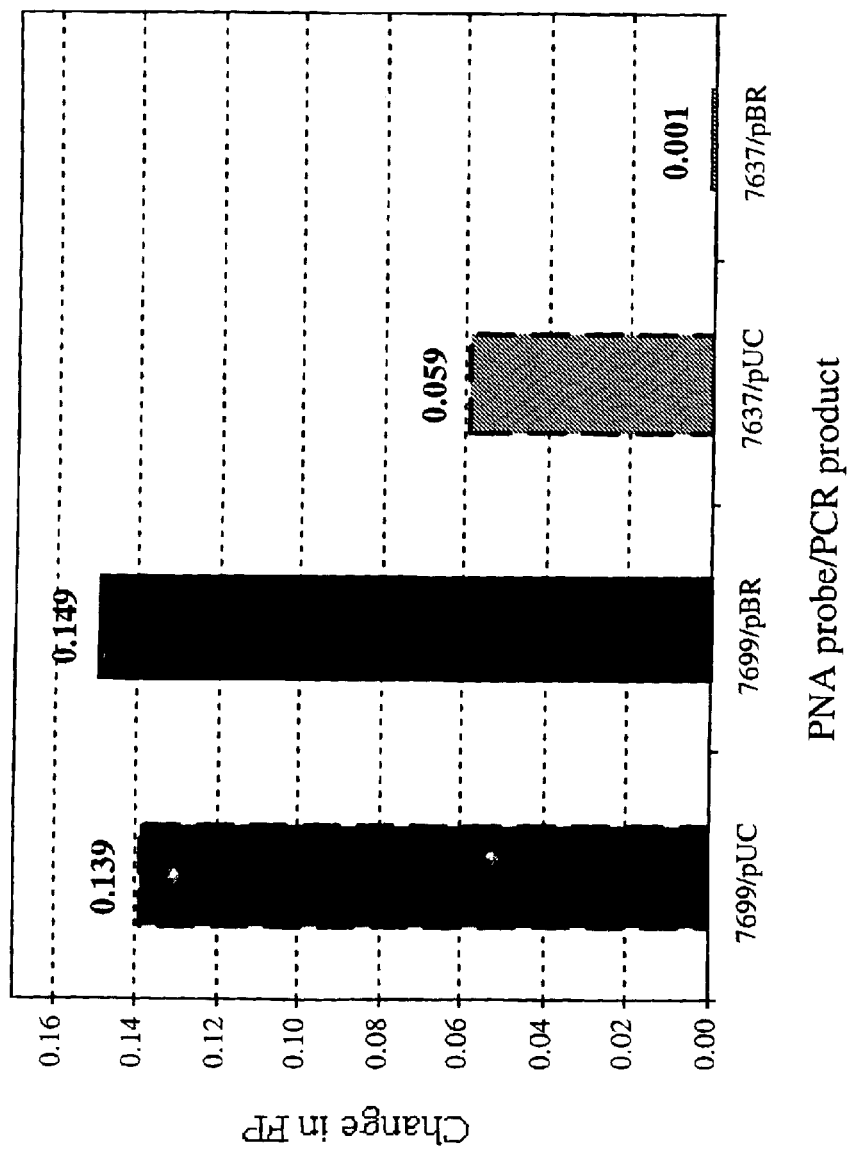
FIG. 3B shows graphs with the results for SNP typing in PCR products, including fluorescein labeled PNA probes. In this experiment, single stranded PCR products were 79 bases long; PNA 7637 is was a 9-mer, matching the pUC product and having a TG mismatch with the pBR product; and PNA 7699 is a 13-mer, fully complementary to both PCR products.
Figure 3C:
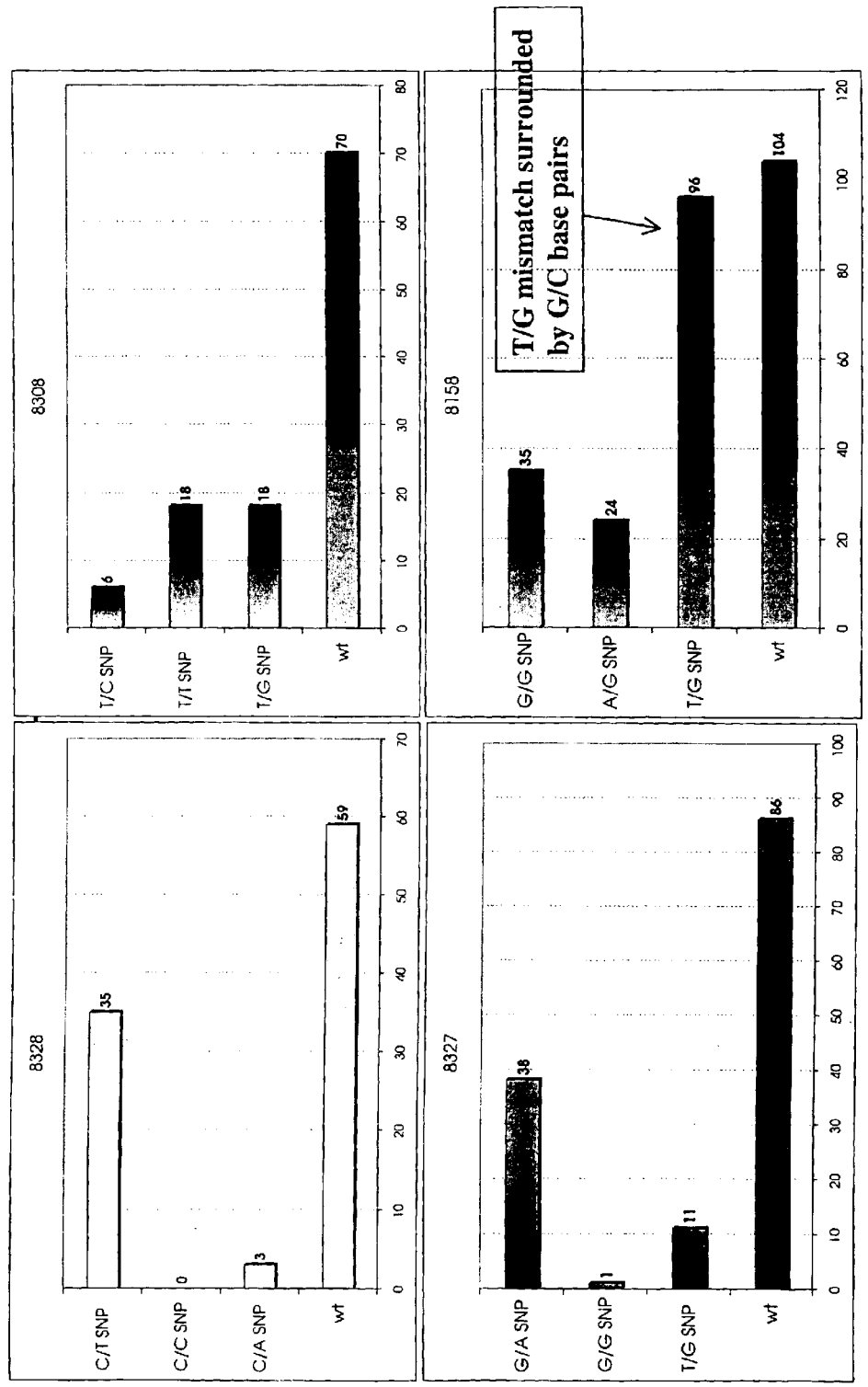
FIG. 3C shows a set of graphs showing SNP discrimination in the absence of polylysine for rhodamine labeled PNAs.
Figure 3D:
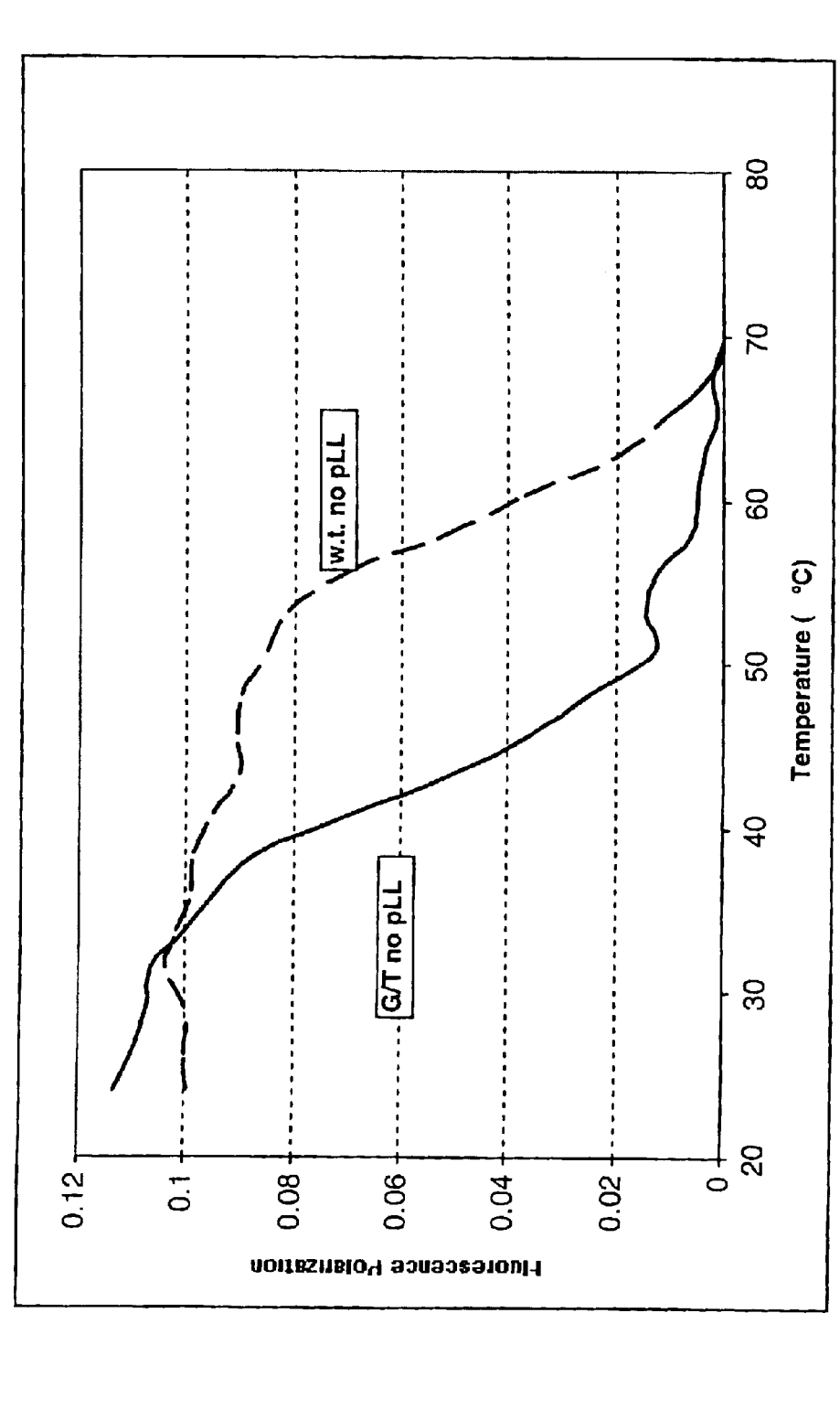
FIG. 3D shows melting curves for rhodamine-labeled probe 8158, including a melting curve for wild-type and G/T SNP targets, in the absence of poly-lysine.

FIG. 2, Panel C schematically shows a histogram depicting the kinetics of PNA/DNA hybridization as detected by FP in the presence of polylysine (see also, Anal. Biochem.

275, 248 (1999)). FIG. 2, Panel D schematically shows several melting curves analyzed by FP. FIG. 2, Panel E shows the effects of mismatch position on PNA/DNA duplex stability with PNA probe 188 (a 9-mer).

Sequences of nucleic acids used for the analysis depicted in FIG. 2 include: 188: Fl-O-CAA-ATA-CTC; 201: Fl-O-TCA-AAT-ACT-CC (SEQ ID NO. 1); 202: Fl-O-GTC-AAA-TAC-TCC-A (SEQ ID NO.2) (also labeled with BODIPY-Fl); 7637: Fl-O-CCT-GTA-GCA; 7638: Fl-O-TGC-TAC-AGG; 7699: Fl-O-CAC-CAC-GAT-GCC-T (SEQ ID NO. 3); 212 5' GCTGGAGTATTTGACCT (SEQ ID NO. 4); 244 5' TTGTTGCCAATGCTACAGGCATCGT (SEQ ID NO. 5); 245 5' TTGTTGCCAATGCTGCAG-GCATCGT (SEQ ID NO. 6); and 247 5' ACGATGCCTG-TAGCATTGGCAACAA (SEQ ID NO. 7). Assay conditions were: 50 nM PNA 188, 50 mM HEPES pH 7.5, 3.3 $\mu$M Poly L-Lysine.

FIG. 3 shows the effects of mismatch position on PNA/DNA duplex stability (i.e., for SNP detection). FIG. 3, Panel A depicts a graph showing the effects of mismatch position on PNA/DNA duplex stability for PNA probe 201 (an 11-mer). Assay conditions included: 50 nM PNA 201, 50 mM HEPES pH 7.5, 3.3 $\mu$M Poly L-Lysine. FIG. 3, Panel B shows graphs with the results for SNP typing in PCR products, including fluorescein labeled PNA probes. In this experiment, single stranded PCR products were 79 bases long; PNA 7637 is was a 9-mer, matching the pUC product and having a TG mismatch with the pBR product; and PNA 7699 is a 13-mer, fully complementary to both PCR products. FIG. 3, Panel C shows a set of graphs showing SNP discrimination in the absence of polylysine for rhodamine labeled PNAs. FIG. 3, Panel D shows melting curves for rhodamine-labeled probe 8158, including a melting curve for wild-type and G/T SNP targets, in the absence of poly-lysine. FIG. 3D shows examples of SNP discrimination using rhodamine labeled PNA probes in a temperature-dependent assay. In these experiments, each PNA probe was hybridized to four different synthetic DNA targets. For each PNA, these targets were identical in sequence with the exception of a single, variable nucleotide position. Thus, for each hybridization experiment, there was a perfect hybrid formed (denoted as wt in FIG. 3D), and three hybrids containing a single mismatched site. The nature of those mismatches are also indicated in the Figure. The changes in FP upon hybrid formation were measured and are shown in the Figure. In all cases, the largest FP increases were seen with the wt targets, while the mismatches had varying degrees of destabilizing effects. As depicted, a single base mismatch dramatically alters the observed FP measurement for, e.g., rhodamine labeled PNAs, even in the absence of poly-lysine.

The sequences of the probes for the analysis presented in FIG. 3 were as follows: 8308: Rh-O-CAA-ATA-CTC (3 GC) (same as Fluorescein labeled 188); 8327: Rh-O-CTA-TGA-CTA (3GC); 8328: Rh-O-ATG-ACT-ATA (2GC); and 8158: Rh-O-CTA-CGC-CAA (5GC).

Figure 4A:
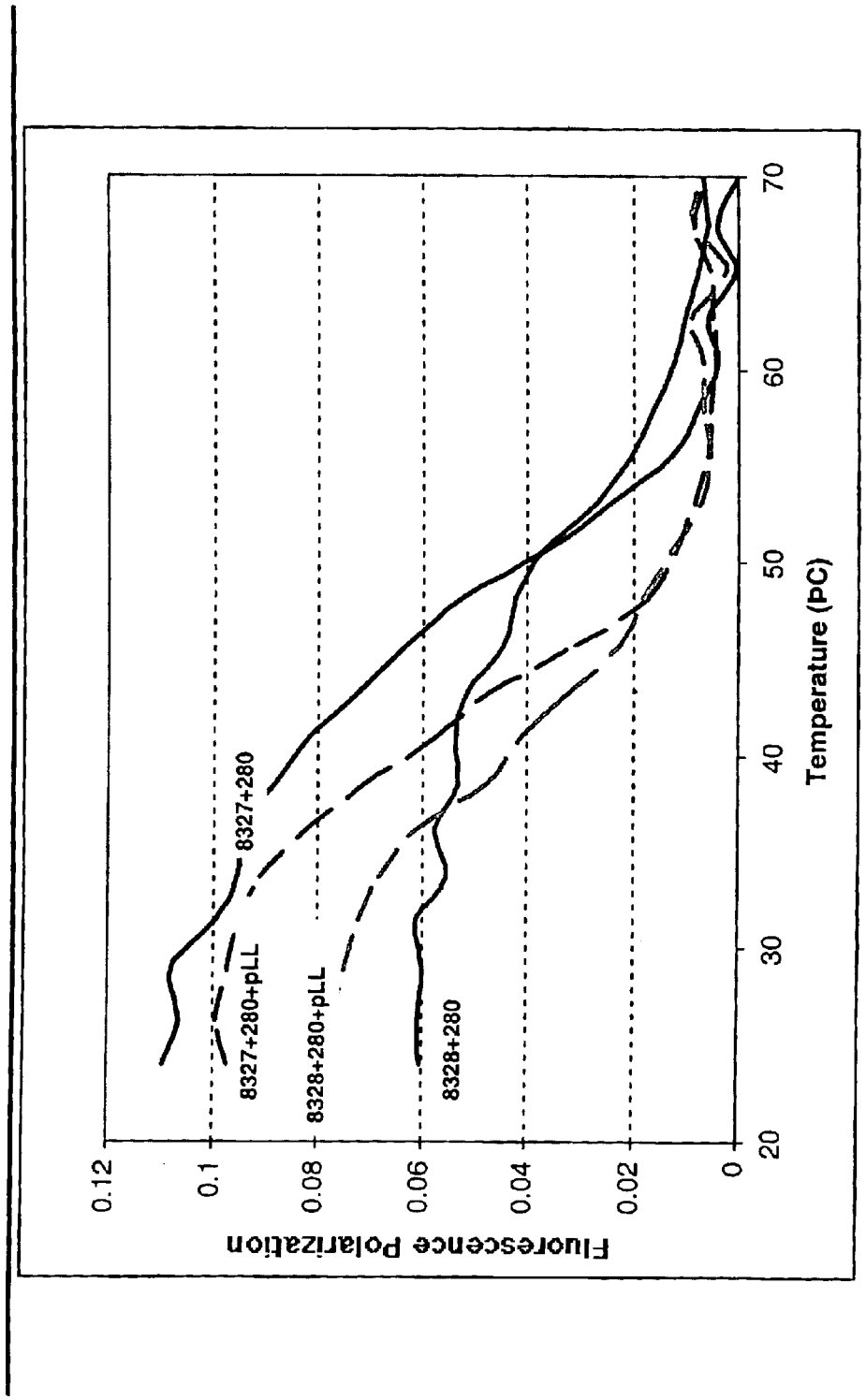
FIG. 4A shows a graph of FP vs. temperature including the effect of poly-Lysine on PNA/DNA duplex stability. Experiments were with rhodamine labeled probes at 50mM HEPES pH 7.5/50mM NaCl, 2$\mu$M PNA, 5$\mu$M DNA Targets, +/− 4 $\mu$M pLL.
Figure 4B:
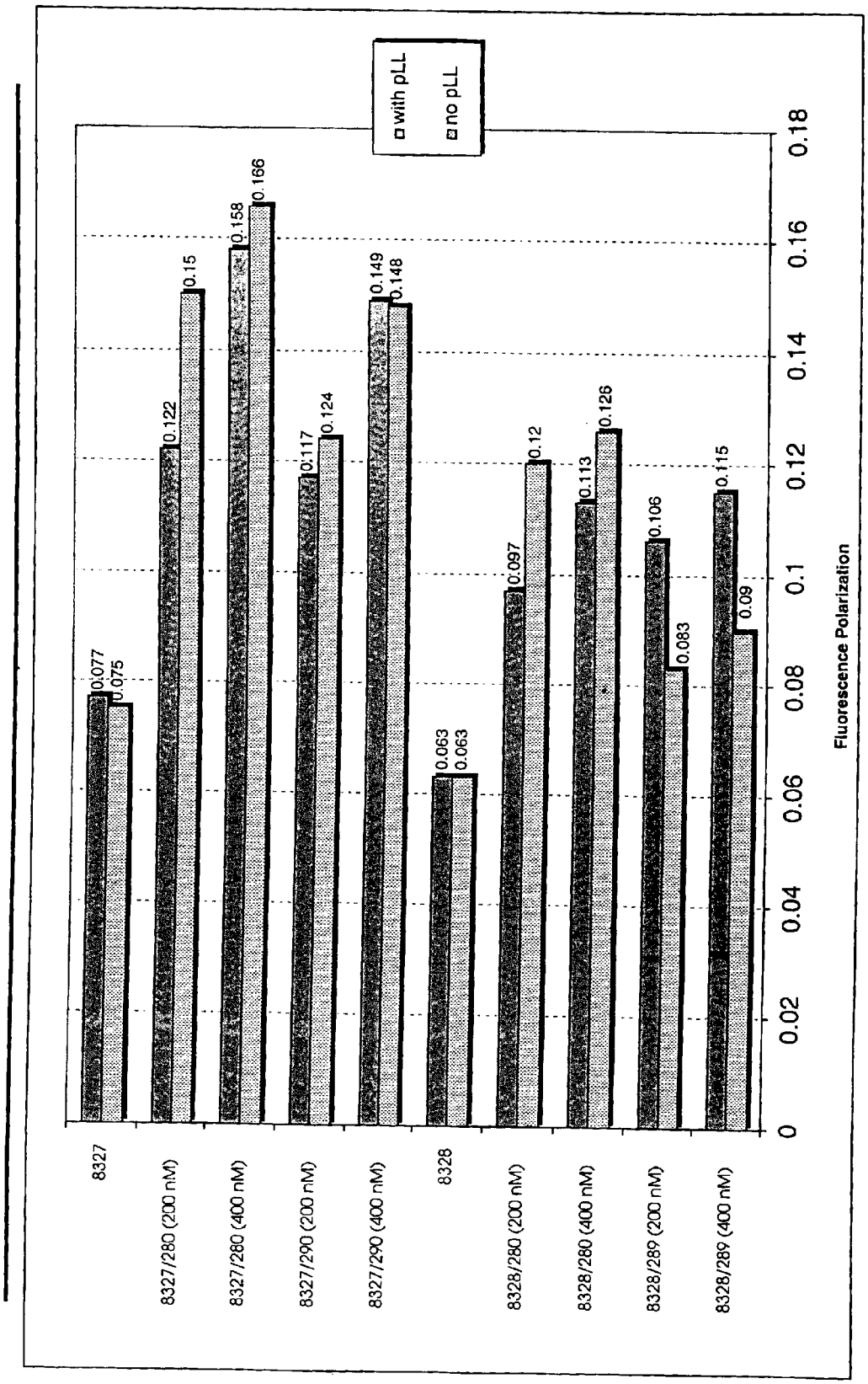
FIG. 4B shows histograms for rhodamine labeled PNAs, including the effect of target size and poly-lysine.

FIG. 4 shows the effect of polylysine on PNA/DNA stability for rhodamine labeled probes. The results presented demonstrate that rhodamine-labeled probes show relatively minor changes in FP upon the addition of polylysine.

In brief, FIG. 4, shows histograms showing the effect of polylysine on DNA/PNA duplex stability, real time detection of T7 gene 6 exonuclease degradation of a PCR product coupled with PNA probe hybridization and the effect of target size and polylysine. Panel A shows a graph of FP vs. temperature including the effect of poly-Lysine on PNA/DNA duplex stability. Experiments were with rhodamine labeled probes at 50 mM HEPES pH 7.5/50 mM NaCl, 2 $\mu$M PNA, 5 $\mu$M DNA Targets, +/−4 $\mu$M pLL. Panel B shows histograms for rhodamine labeled PNAs, including the effect of target size and poly-lysine. Panel C shows real-time detection of T7 gene 6 exonuclease degradation of a PCR product coupled with PNA probe hybridization. One of the PCR strands contains four phosphorothioates at its 5' end, making it resistant to T7 gene 6 exonuclease. The enzyme hydrolyses the opposite strand to generate a single-stranded template to which the PNA probe hybridizes. The reactions were carried out in PCR buffer. The DNA targets were a 22mer (280) and 9mers (289, 290). PNA probes were 200 nM in 50 mM HEPES pH 7.5, 50 mM NaCl, with Poly-lysine at 0 or 4 $\mu$M.

Figure 4C:
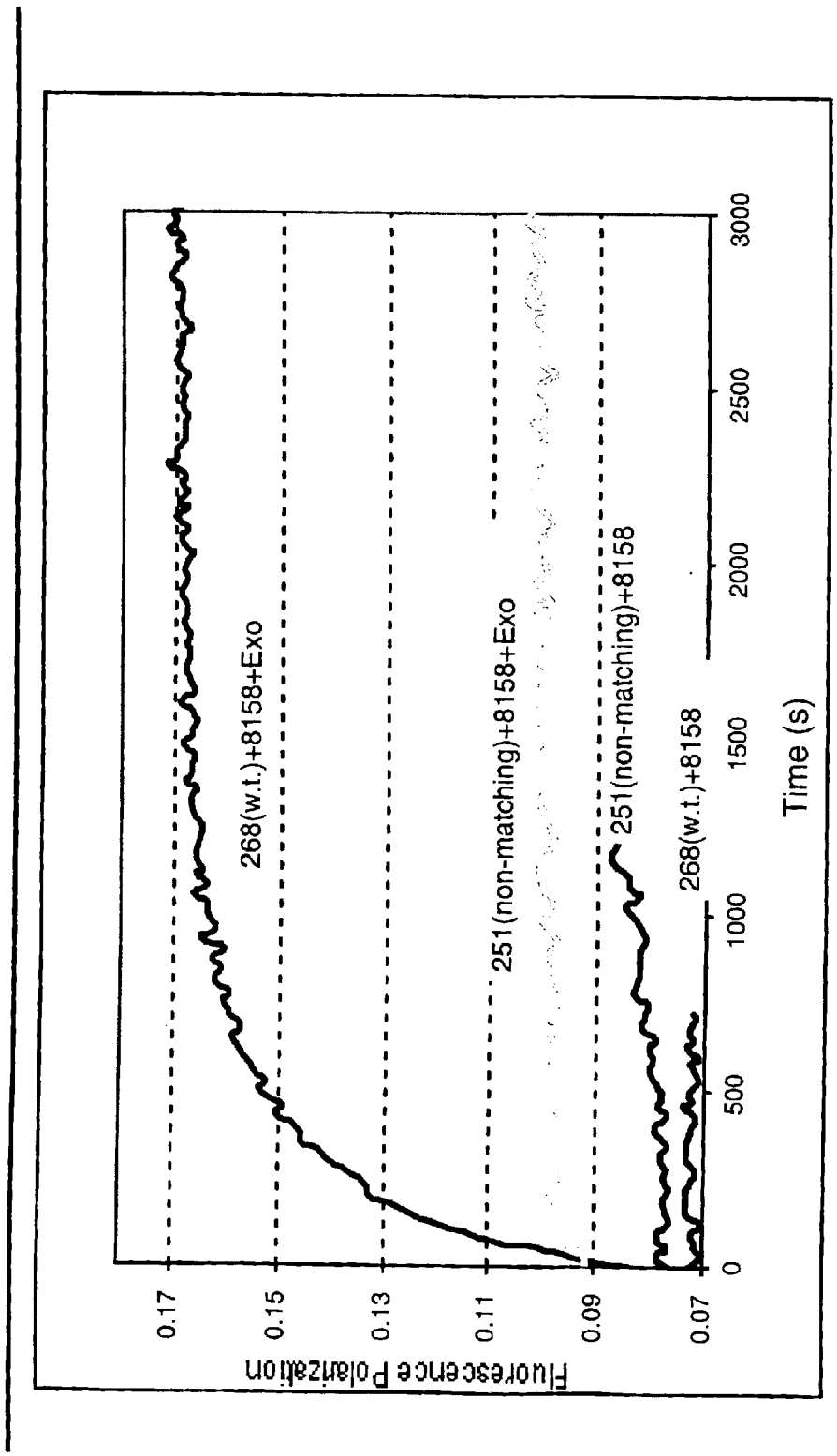
FIG. 4C shows real-time detection of T7 gene 6 exonuclease degradation of a PCR product coupled with PNA probe hybridization. One of the PCR strands contains four phosphorothioates at its 5' end, making it resistant to T7 gene 6 exonuclease. The enzyme hydrolyses the opposite strand to generate a single-stranded template to which the PNA probe hybridizes. The reactions were carried out in PCR buffer. The DNA targets were a 22mer (280) and 9mers (289, 290). PNA probes were 200 nM in 50 mM HEPES pH 7.5, 50 mM NaCl, with Poly-lysine at 0 or 4 $\mu$M.

In the experiments depicted in FIG. 4C, DNA target 268 is an 84 bp, double stranded PCR product which contains the following sequence: 5' . . . TTGGCGTAG . . . . This sequence is fully complementary to the PNA probe used in this experiment, 8158, which has the following sequence: Rh-CTACGCCAA. The second ds PCR product, 251, is also an 84 bp molecule which has no complementary regions to the PNA probe 8158. Both PCR products were generated using one phosphorothioated PCR primer and one regular primer. Following the PCR amplification, the PNA probe was added to solutions containing one or the other PCR product and FP values were measured. These values were almost the same as those seen for the free probe, because no hybridization occurs under these conditions.

At this stage, T7 gene 6 exonuclease was added to the solution. The enzyme hydrolyzes only the regular, non-phosphorothioated strand of the PCR products, generating single stranded target molecules. The PNA probe hybridizes to the resulting complementary region within 268 and the FP value increases significantly. No change is seen with 251, which does not have regions to which hybridization occurs.

This example shows that FP is a useful tool for the detection of PNA/DNA hybrid formation in, e.g., a homogeneous solution. It also shows that when PNA probes are labeled with fluorescein, the addition of poly-lysine significantly increases the useful range of the assay. Surprisingly, however, the use of rhodamine-labeled probes, as well as BODIPY-labeled PNAs, resulted in significant FP responses upon hybridization, even in the absence of polylysine. The high sensitivity of PNA probes towards single nucleotide polymorphisms combined with the simplicity of the fluorescence polarization detection method can be used, e.g., as a method of SNP detection.

While the foregoing invention has been described in some detail for purposes of clarity and understanding, it will be clear to one skilled in the art from a reading of this disclosure that various changes in form and detail can be made without departing from the scope of the invention. For example, all the techniques and apparatus described above can be used in various combinations which will be apparent upon complete review of the foregoing disclosure and following claims.

The disclosure of U.S. Ser. No. 60/203,723 is incorporated by reference in its entirety for all purposes. In addition, all publications, patents, patent applications, other documents, internet citations, CD-ROM citations and other publicly accessible information listed herein are hereby incorporated by reference for all purposes, as if each individual publication, patent, patent application or other document was specifically and individually indicated to be incorporated by reference.

Although the present invention has been described in some detail by way of illustrations and examples for purposes of clarity and understanding, it will be apparent that certain changes and modifications may be practiced within the scope of the appended claims.

What is claimed is:

1. A method for detecting a nucleic acid, the method comprising: contacting a first nucleic acid to a second nucleic acid, which second nucleic acid comprises a neutral or positively charged fluorescent label when hybridized to the first nucleic acid; and, detecting fluorescence polarization of the resulting mixture of first and second nucleic acids.

2. A method for detecting a nucleic acid, the method comprising:

contacting a first nucleic acid to a second nucleic acid, which second nucleic acid comprises a neutral or positively charged fluorescent label; and, detecting fluorescence polarization of the resulting mixture of first and second nucleic acids, wherein the fluorescence polarization is increased by less than about 50% by the addition of polylysine to the first and second nucleic acid.

3. The method of claim 1, wherein the mixture of first and second nucleic acids is present in a composition which is substantially free of polyion.

4. The method of claim 3, wherein the composition comprises less than 1 $\mu$M polyion.

5. The method of claim 1, wherein a rotational diffusion rate of a duplex of the first and second nucleic acid is less than a rotational diffusion rate of the first or second nucleic acid.

6. The method of claim 5, wherein the fluorescence polarization of unduplexed first or second nucleic acid is at least 50% different than the fluorescence polarization of the duplexed nucleic acid.

7. The method of claim 1, wherein the first or second nucleic acid comprises one or more of: DNA, RNA, LNA, a DNA analogue, an RNA analogue or a PNA.

8. The method of claim 1, wherein one or more of the nucleic acids is nuclease resistant.

9. The method of claim 1, wherein the fluorescent label comprises rhodamine or BODIPY.

10. The method of claim 1, wherein the first nucleic acid is a DNA and the second nucleic acid is a PNA which comprises a rhodamine label.

11. The method of claim 1, wherein the first or second nucleic acids comprise at least a region which is single-stranded.

12. The method of claim 11, wherein the first and second nucleic acid are perfectly complementary.

13. The method of claim 11, wherein the first and second nucleic acid comprise at least one non-complementary nucleotide when aligned for maximum complementarity.

14. The method of claim 11, further comprising determining from the fluorescence polarization detection whether the first and second nucleic acids are duplexed.

15. The method of claim 11, further comprising determining the extent to which the first and second nucleic acids are duplexed from the fluorescence polarization detection.

16. The method of claim 1, wherein the first and second nucleic acids hybridize in solution prior to detection of fluorescence polarization.

17. The method of claim 16, comprising comparing the detected fluorescence polarization to a fluorescence polarization measurement of either the first or the second nucleic acid alone in solution.

18. The method of claim 16, comprising comparing the detected fluorescence polarization to a fluorescence polarization measurement of either the first or the second nucleic acid hybridized to a third nucleic acid.

19. The method of claim 18, wherein the third nucleic acid is perfectly complementary to either the first or the second nucleic acid.

20. The method of claim 18, wherein the third nucleic acid is not perfectly complementary to either the first or the second nucleic acid.

21. The method of claim 18, wherein the third nucleic acid is unrelated in sequence to either the first or the second nucleic acid.

22. The method of claim 16, comprising detecting fluorescence polarization during hybridization of the first and second nucleic acid.

23. The method of claim 22, further comprising determining the fluorescence polarization as a function of time during hybridization of the first and second nucleic acid.

24. The method of claim 23, further comprising plotting a histogram of the fluorescence polarization as a function of time.

25. A method of identifying the presence of a subsequence of nucleotides in a target nucleic acid, the method comprising:

contacting the target nucleic acid sequence with a labeled nucleic acid probe, which labeled nucleic acid probe comprises a neutral or positively charged label comprising a fluorophore to form a first reaction mixture; and, detecting the level of fluorescence polarization of the first reaction mixture, wherein the probe comprises the labeled fluorophore when hybridized to the target nucleic acid.

26. The method of claim 25, wherein the target nucleic acid sequence comprises at least one locus for a single nucleotide polymorphism.

27. The method of claim 26, wherein the nucleic acid probe is complementary to one allele of the single nucleotide polymorphism in the target nucleic acid sequence.

28. The method of claim 25, comprising contacting a plurality of additional target nucleic acids with a plurality of additional labeled nucleic acid probes, which additional labeled nucleic acid probes individually comprise a neutral or positively charged label comprising a fluorophore to form a plurality of additional reaction mixtures; and, detecting the level of fluorescence polarization of the plurality of additional reaction mixtures.

29. The method of claim 28, wherein the plurality of additional target nucleic acids individually comprise at least one locus for a single nucleotide polymorphism.

30. The method of claim 29, wherein the plurality of additional nucleic acid probes are individually complementary to at least one allele of each of the single nucleotide polymorphisms in the plurality of target nucleic acid sequences.

31. The method of claim 30, wherein the plurality of additional target nucleic acids are derived from a single species, variety, cultivar, cell, virus, or organism.

32. The method of claim 31, wherein identification of the single nucleotide polymorphisms provides a single nucleotide polymorphism genotype for the species, variety, cultivar, cell, virus or organism.

33. The method of claim 25, wherein the fluorescence polarization is increased by less than about 50% by the addition of polylysine to the target and probe nucleic acids.

34. The method of claim 25, wherein the target and probe nucleic acids are present in a composition which is substantially free of polyion.

35. The method of claim 34, wherein the composition comprises less than 1 $\mu$M polyion.

36. The method of claim 25, wherein a rotational diffusion rate of a duplex of the target and probe nucleic acids is less than a rotational diffusion rate of the target or probe nucleic acids.

37. The method of claim 36, wherein the fluorescence polarization of the probe which is duplexed to the target is at least 50% different than the fluorescence polarization of the probe when not duplexed to the target.

38. The method of claim 25, wherein the target or probe nucleic acids comprise one or more of: DNA, RNA, LNA, a DNA analogue, an RNA analogue or a PNA.

* * * * *

SEQUENCE LISTING

<160> NUMBER OF SEQ ID NOS: 7

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 1
tcaaatactc c                                                              11

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 2
gtcaaatact cca                                                            13

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 3
caccacgatg cct                                                            13

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 4
gctggagtat ttgacct                                                        17

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 5
ttgttgccaa tgctacaggc atcgt                                               25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 6

-continued ttgttgccaa tgctgcaggc atcgt                              25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      PNA

<400> SEQUENCE: 7
acgatgcctg tagcattggc aacaa                              25